United States Patent
Park et al.

(10) Patent No.: US 11,181,531 B2
(45) Date of Patent: Nov. 23, 2021

(54) BIOINFORMATICS PLATFORM FOR HIGH-THROUGHPUT IDENTIFICATION AND QUANTIFICATION OF O-GLYCOPEPTIDE

(71) Applicant: Korea Basic Science Institute, Daejeon (KR)

(72) Inventors: Gun Wook Park, Cheongju-si (KR); Jong Shin Yoo, Seoul (KR); Jin Young Kim, Cheongju-si (KR); Ju Yeon Lee, Daejeon (KR); Hyun Kyoung Lee, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 678 days.

(21) Appl. No.: 16/078,333

(22) PCT Filed: Dec. 15, 2017

(86) PCT No.: PCT/KR2017/014856
§ 371 (c)(1),
(2) Date: Aug. 21, 2018

(87) PCT Pub. No.: WO2019/066147
PCT Pub. Date: Apr. 4, 2019

(65) Prior Publication Data
US 2020/0408774 A1   Dec. 31, 2020

(30) Foreign Application Priority Data
Sep. 26, 2017   (KR) .................... 10-2017-0124401

(51) Int. Cl.
*G01N 33/68*   (2006.01)
*G16B 50/00*   (2019.01)

(52) U.S. Cl.
CPC ......... *G01N 33/6848* (2013.01); *G16B 50/00* (2019.02); *G01N 2560/00* (2013.01)

(58) Field of Classification Search
None
See application file for complete search history.

(56) References Cited

U.S. PATENT DOCUMENTS

| 8,227,251 B2 | 7/2012 | Ranish et al. |
| 2008/0050833 A1 | 2/2008 | Smith et al. |
| 2015/0186595 A1* | 7/2015 | Park ..................... H01J 49/004 506/8 |

FOREIGN PATENT DOCUMENTS

| KR | 10-2012-0124767 | 11/2012 |
| KR | 10-1341591 | 12/2013 |

OTHER PUBLICATIONS

Eshghi et al. (2016) Scientific Reports, Article No. 37189, pp. 1-8.
(Continued)

*Primary Examiner* — Xiaoyun R Xu
(74) *Attorney, Agent, or Firm* — Leydig, Voit & Mayer, Ltd.

(57) ABSTRACT

The present invention relates to a bioinformation processing analysis method for the identification and quantification of O-linked glycopeptide using high resolution mass spectrum. Particularly, according to the bioinformation processing analysis method of the present invention, the quantitative changes of O-linked glycopeptide containing non-informed sugar chains included in various samples can be efficiently and accurately analyzed; the prediction or diagnosis of disease including cancer can be made easy by using a high resolution mass spectrometer; or the investigation of O-linked glycopeptide structure of a therapeutic glycoprotein can be efficiently achieved.

12 Claims, 23 Drawing Sheets
Specification includes a Sequence Listing.

(56) References Cited

OTHER PUBLICATIONS

Tsai et al. (2017) Mass Spectrometry (Epub: 2017.2.24.) 6(2):S0064, pp. 1-5.

* cited by examiner

[Figure 1]
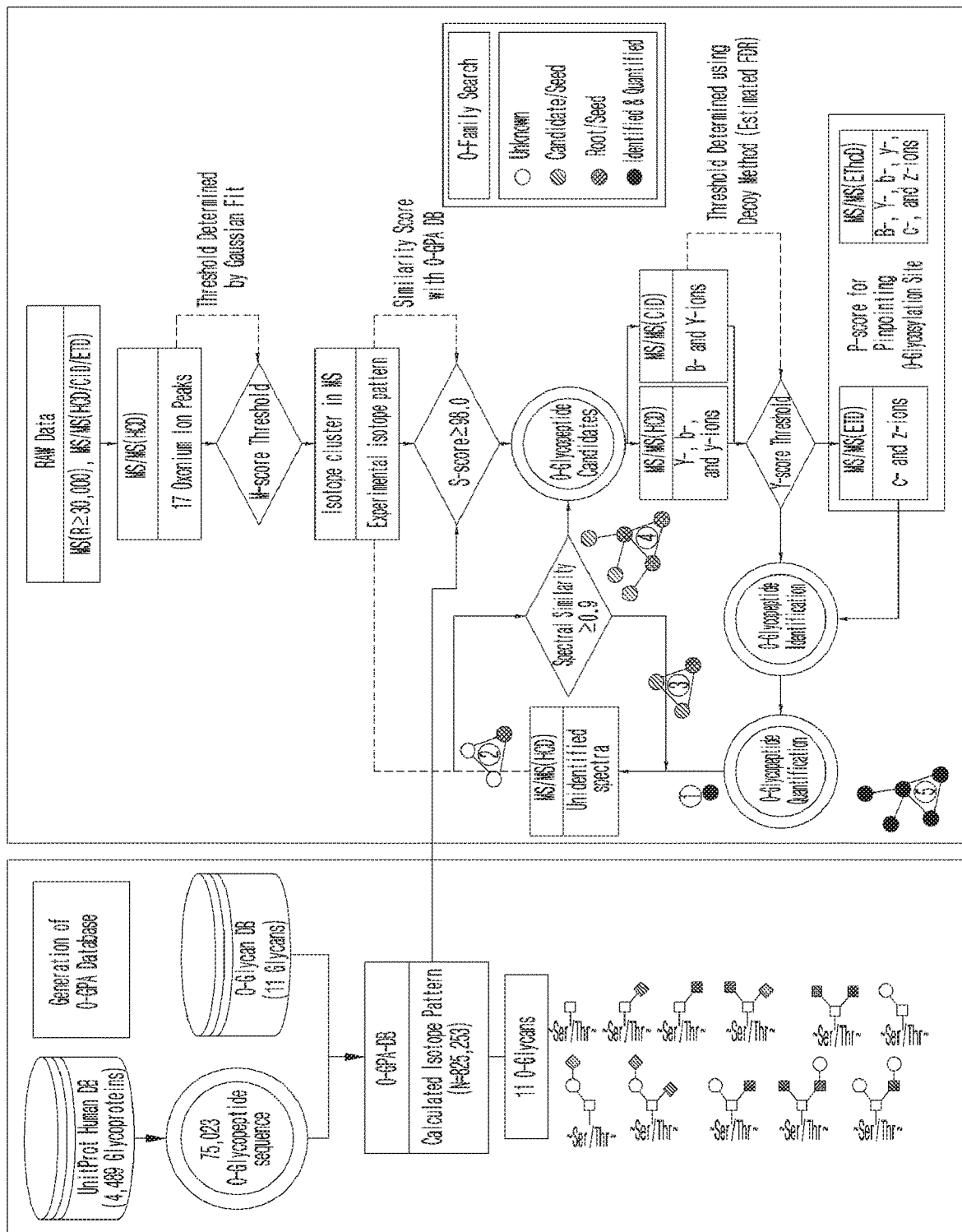

[Figure 2]
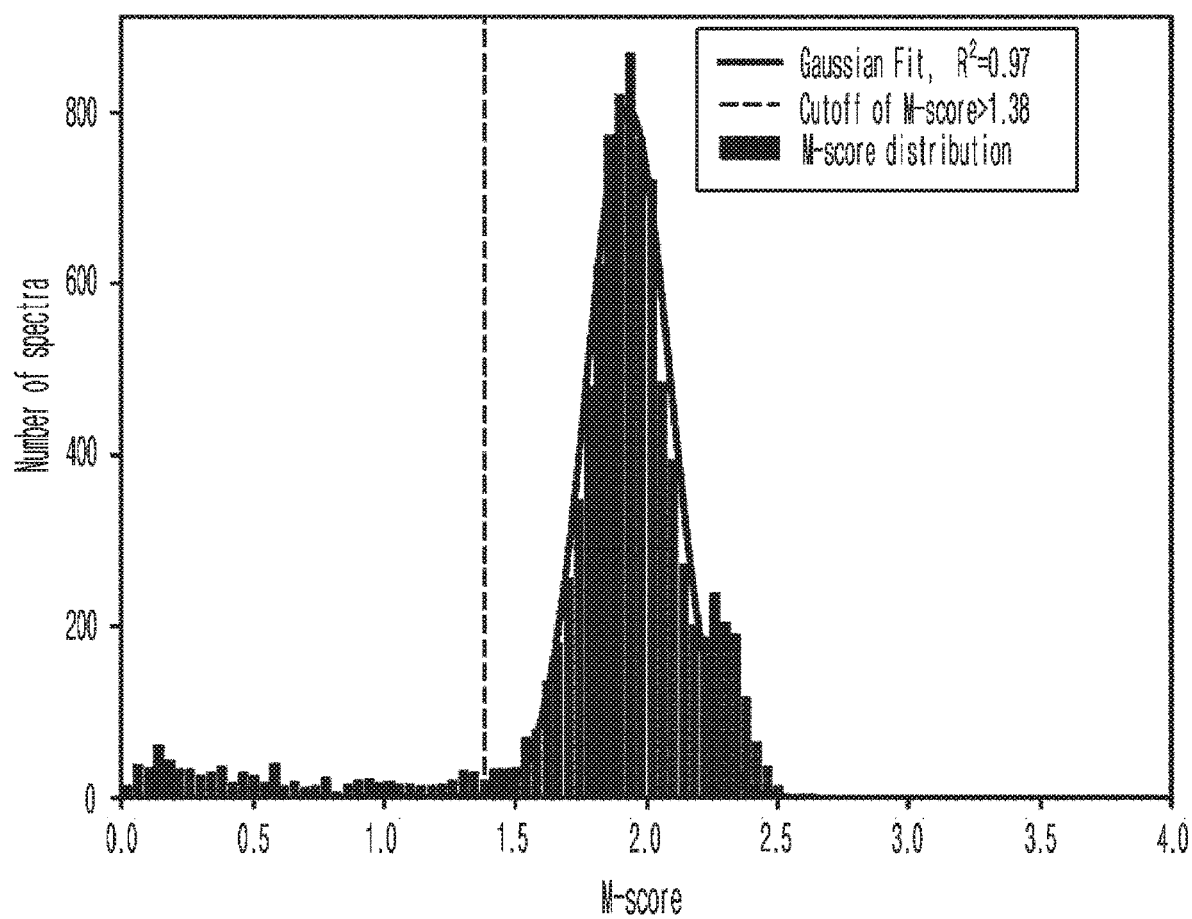

[Figure 3]
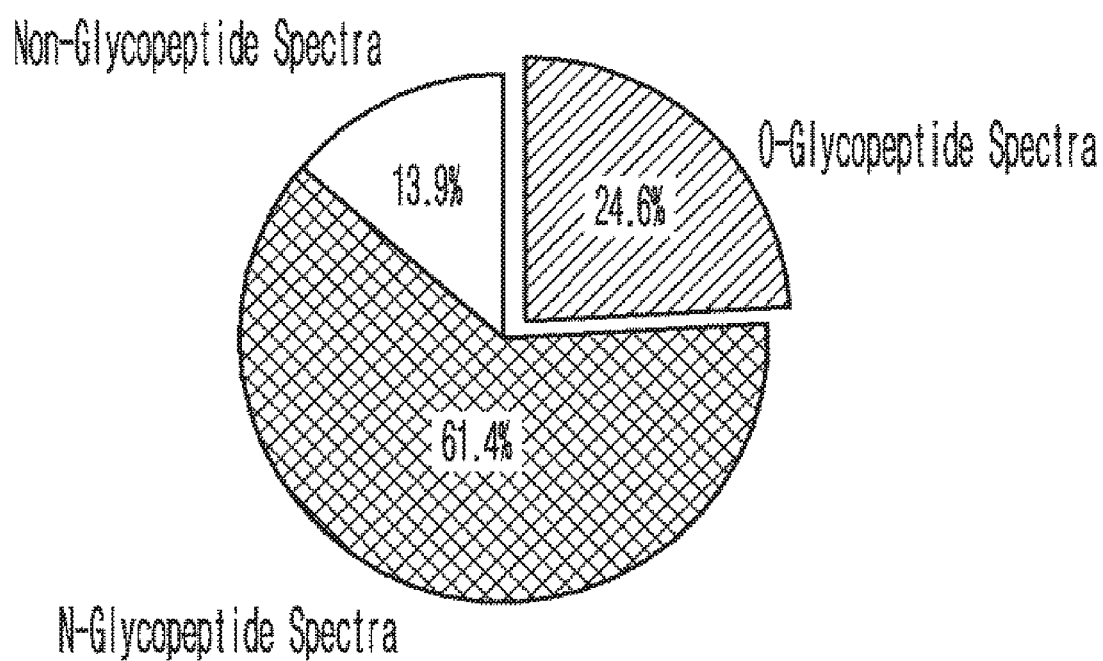

[Figure 4]
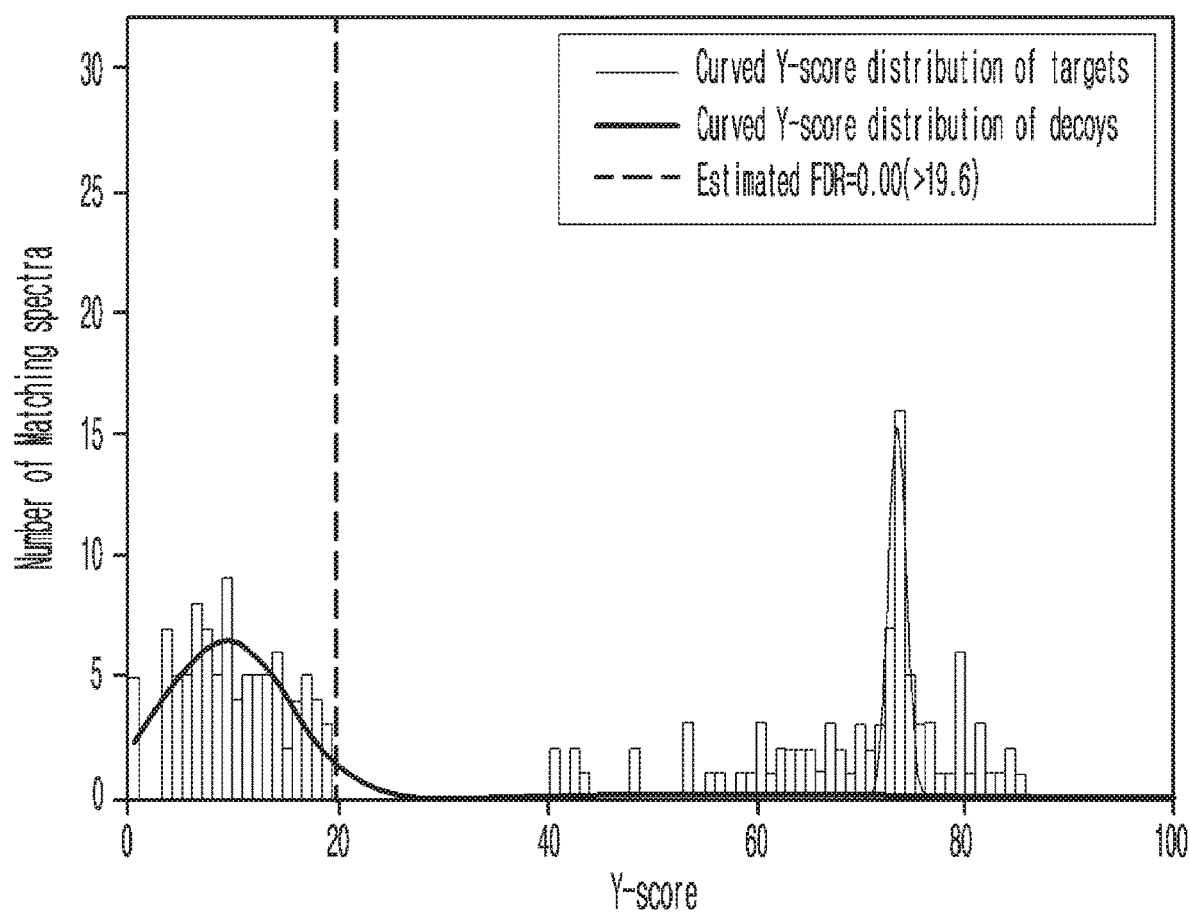

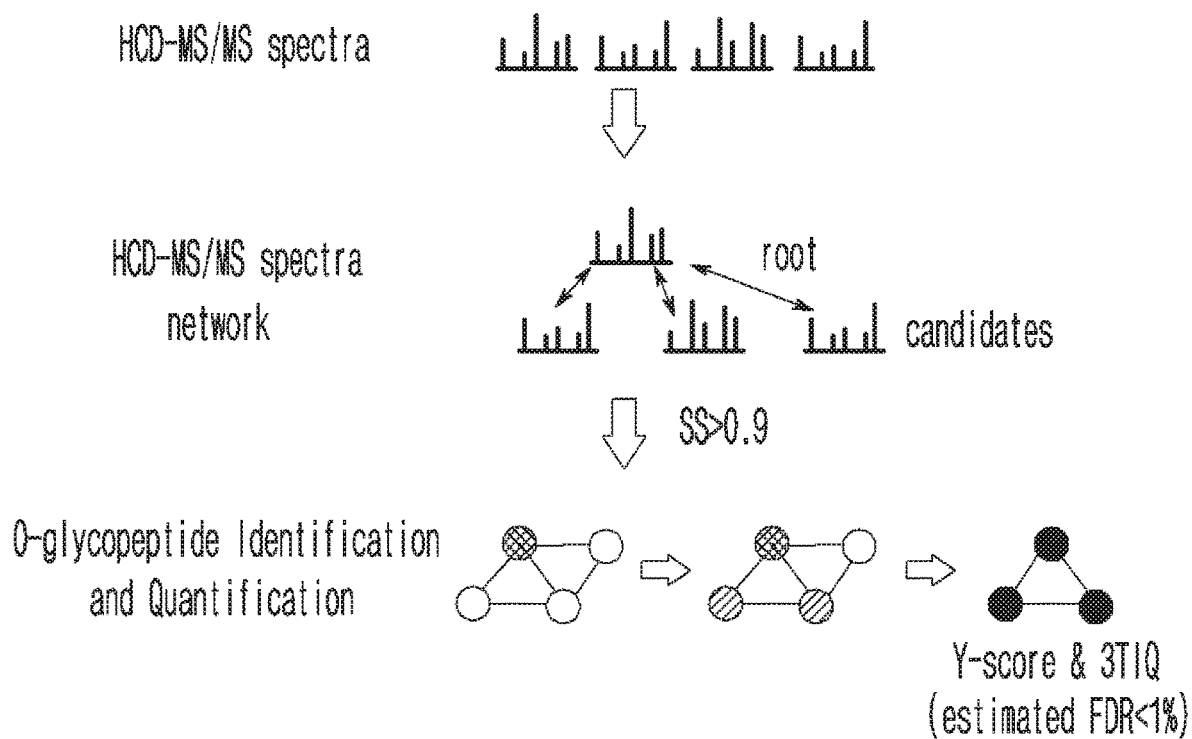
[Figure 5]

[Figure 6a]
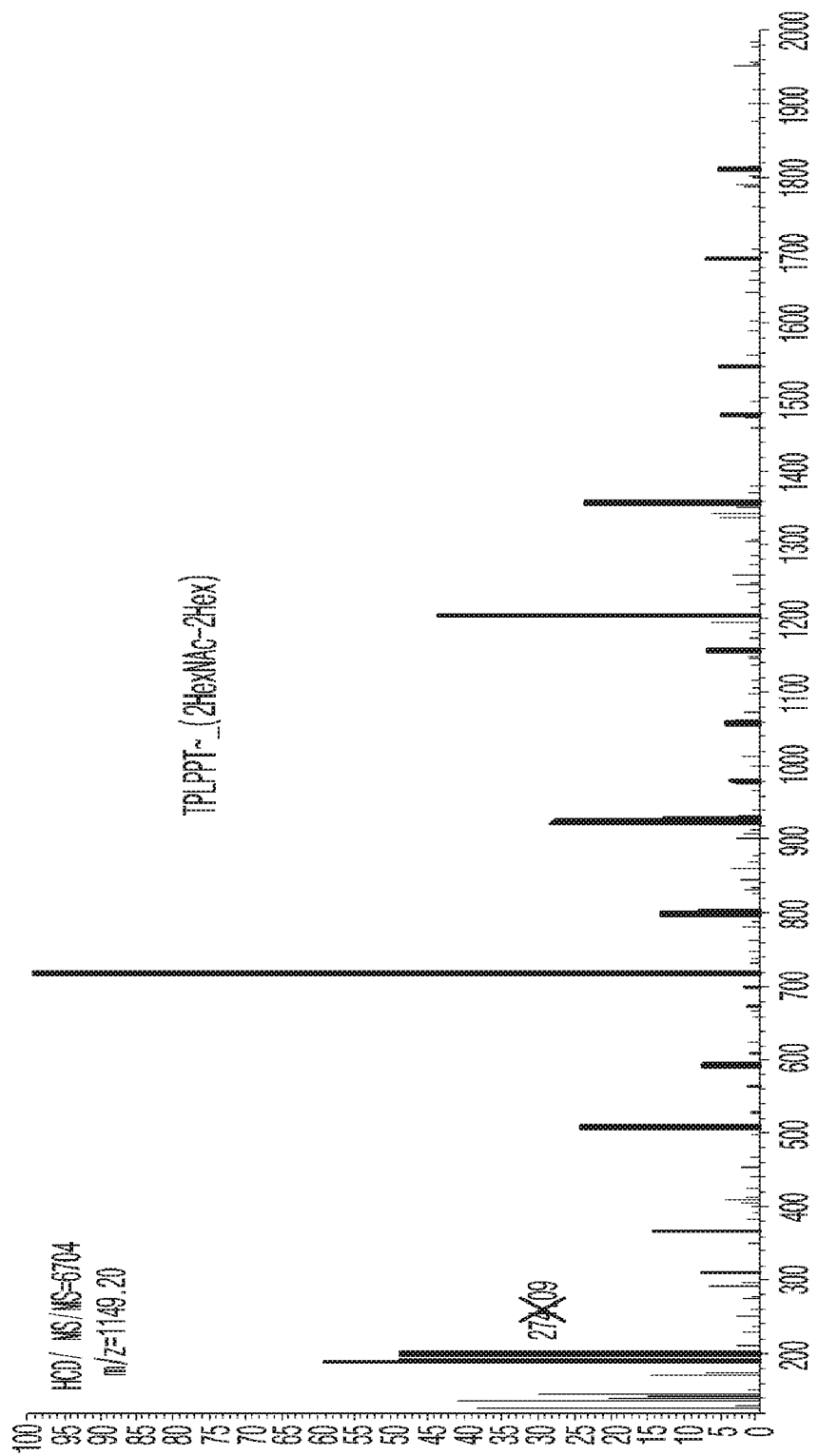

[Figure 6b]
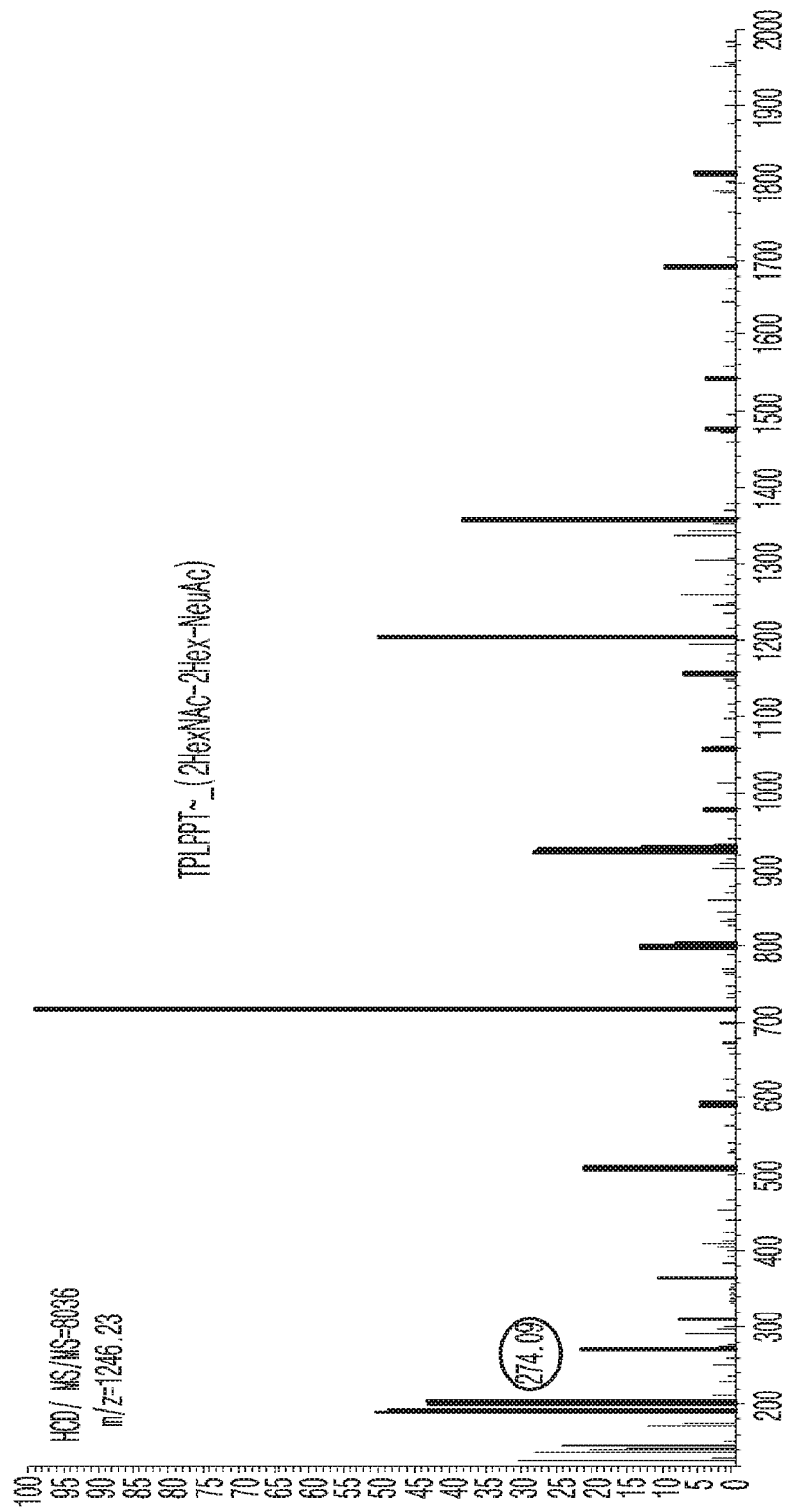

[Figure 7]
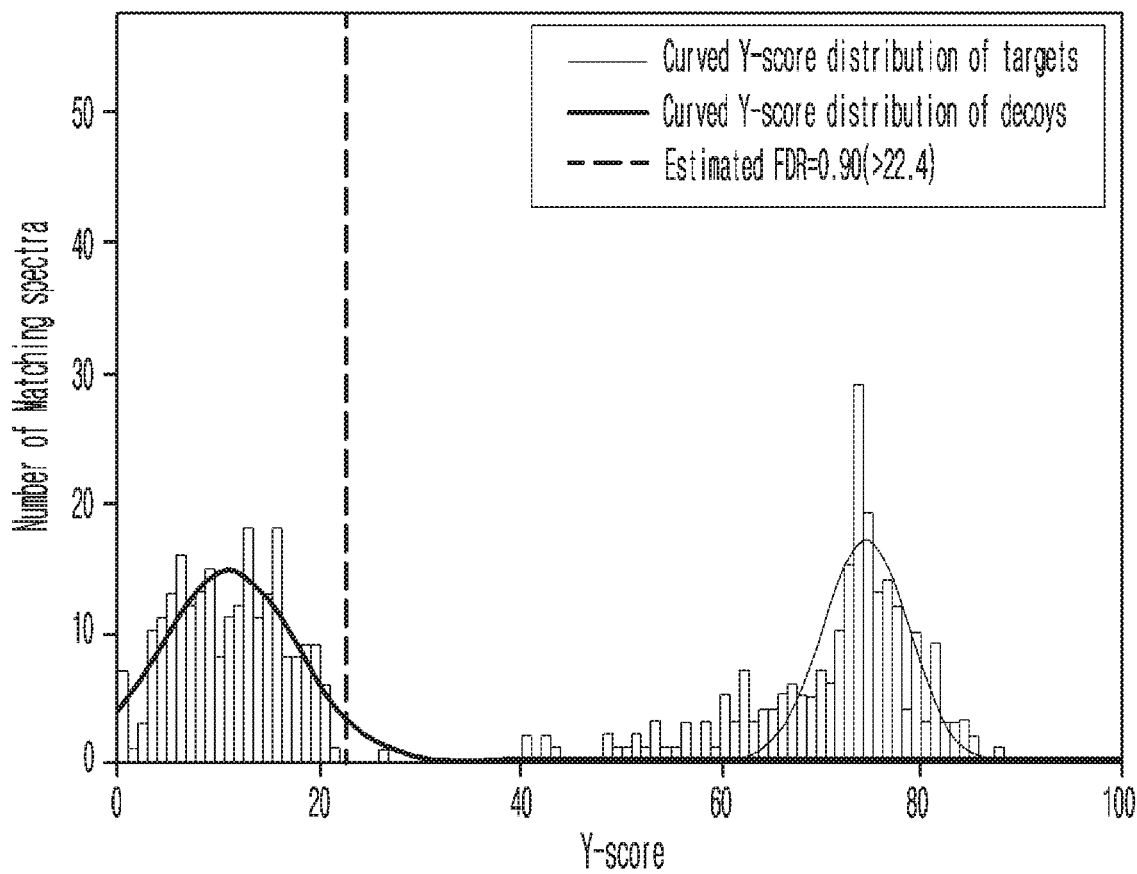

[Figure 8a]
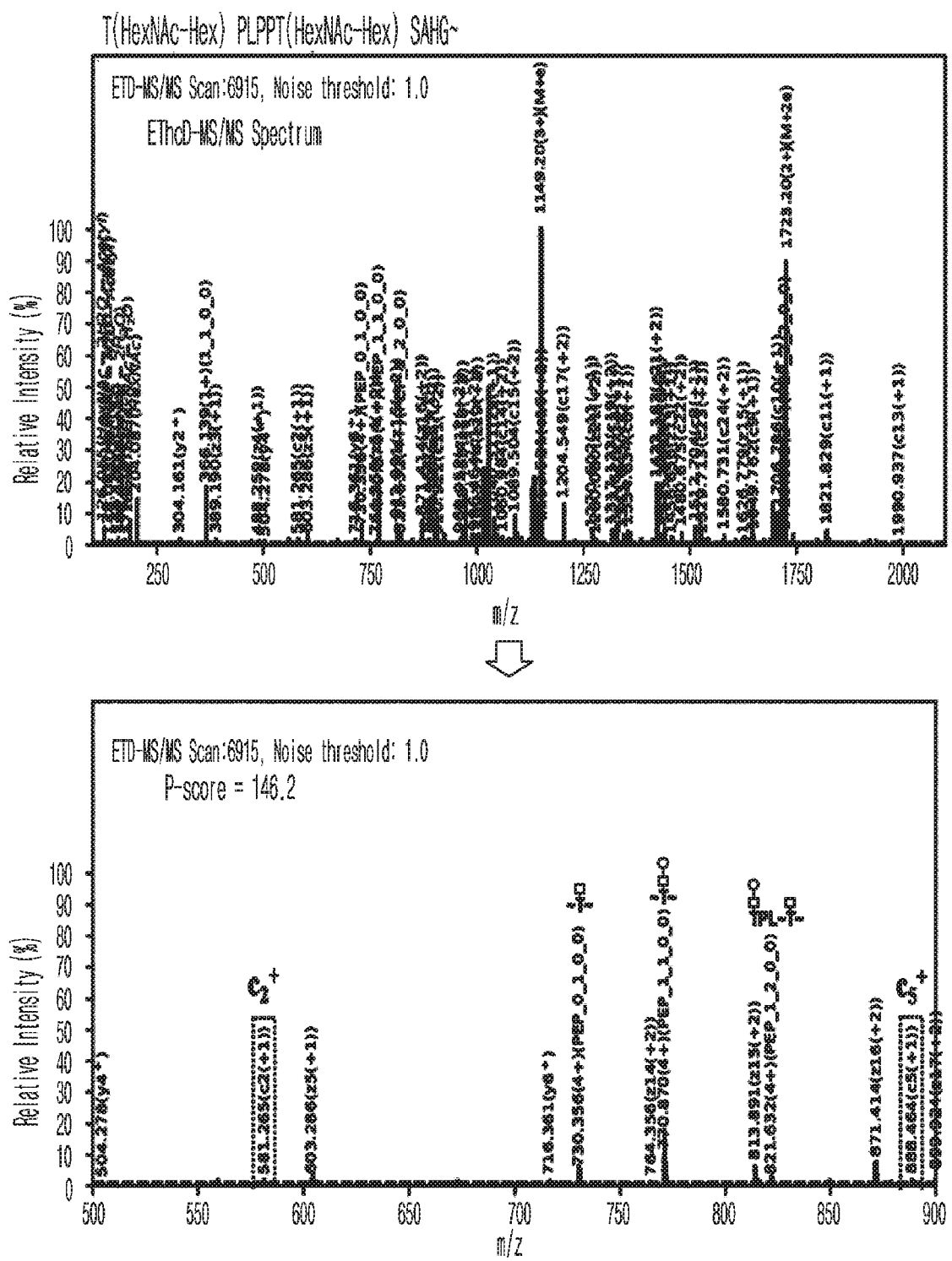

[Figure 8b]
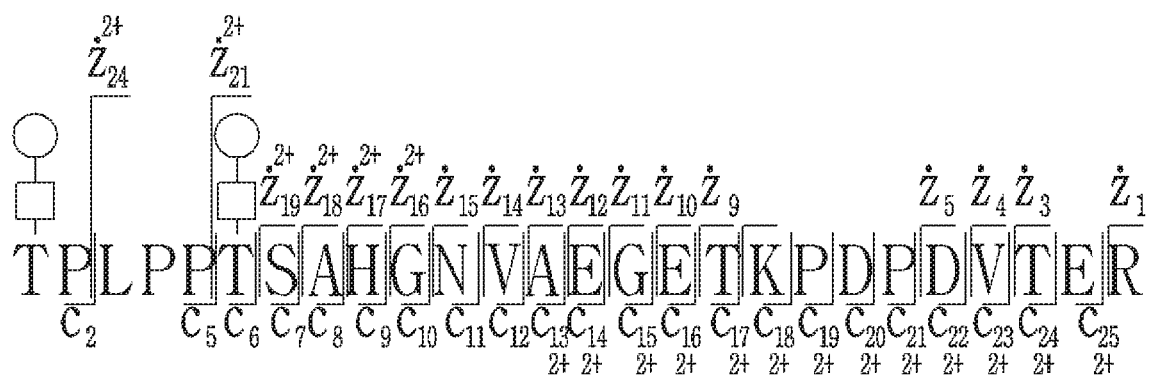

[Figure 9a]
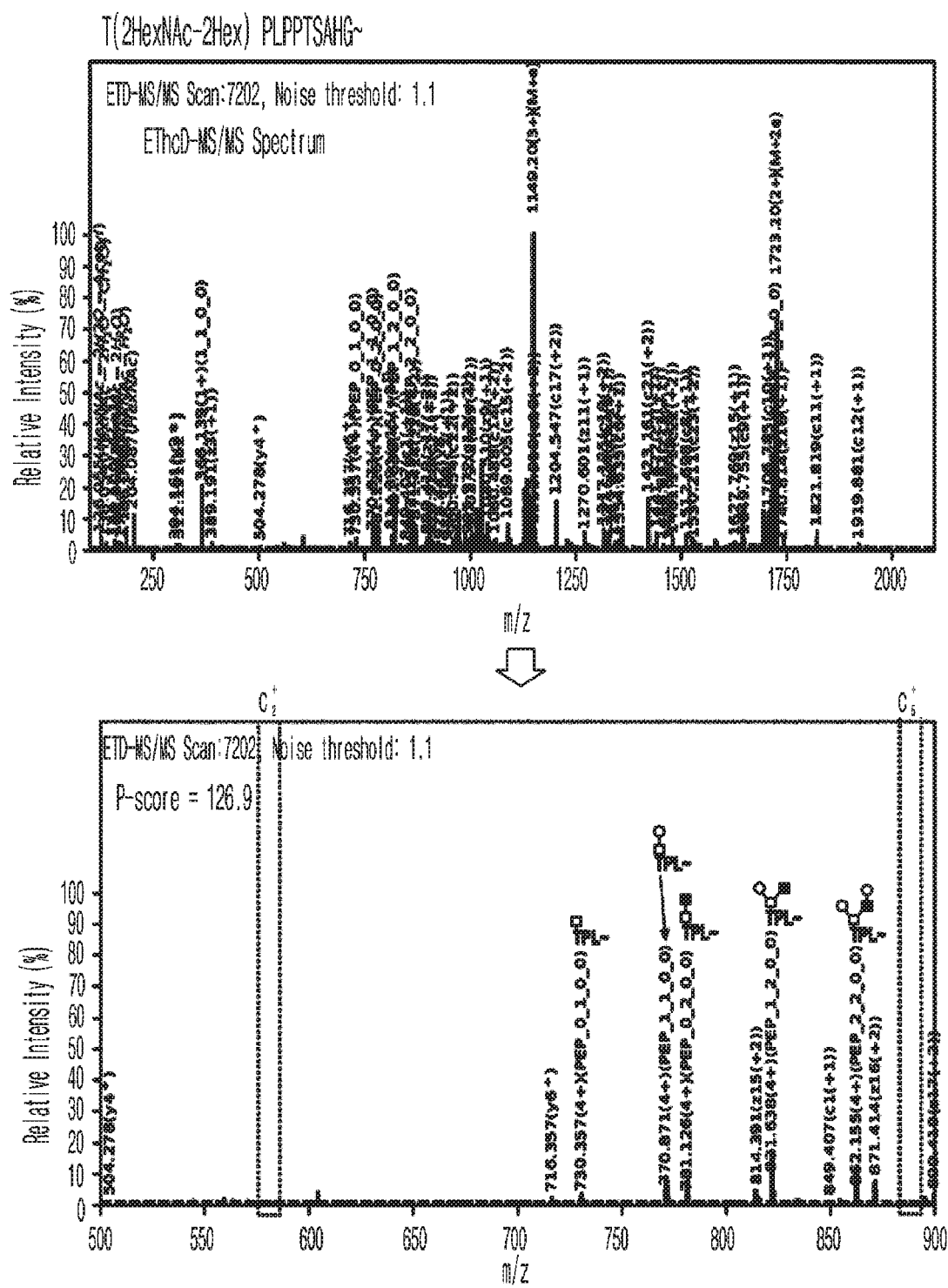

[Figure 9b]
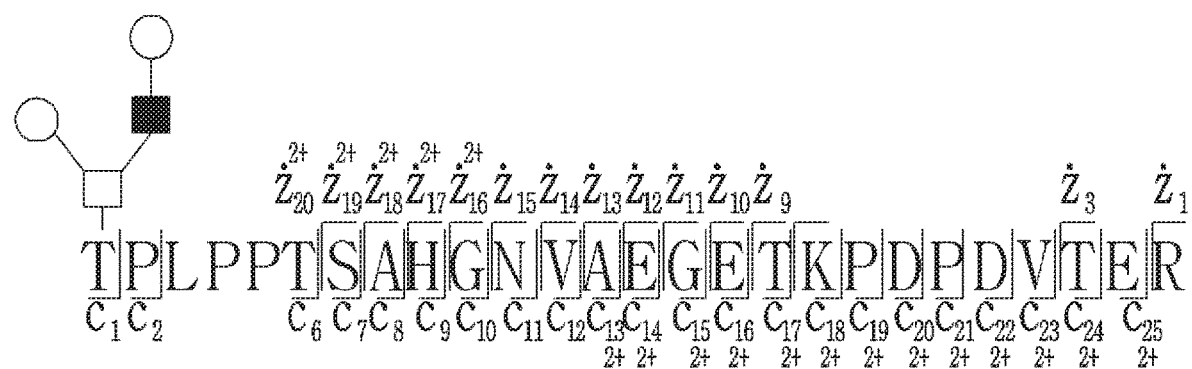

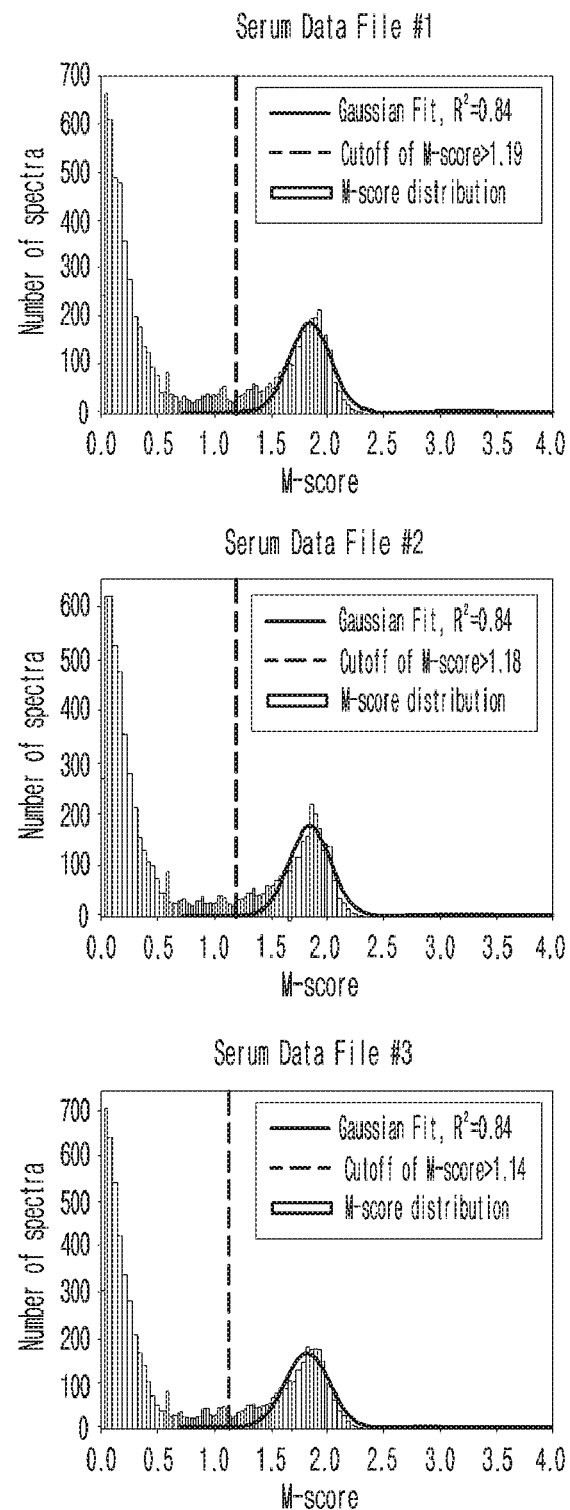
[Figure 10a]

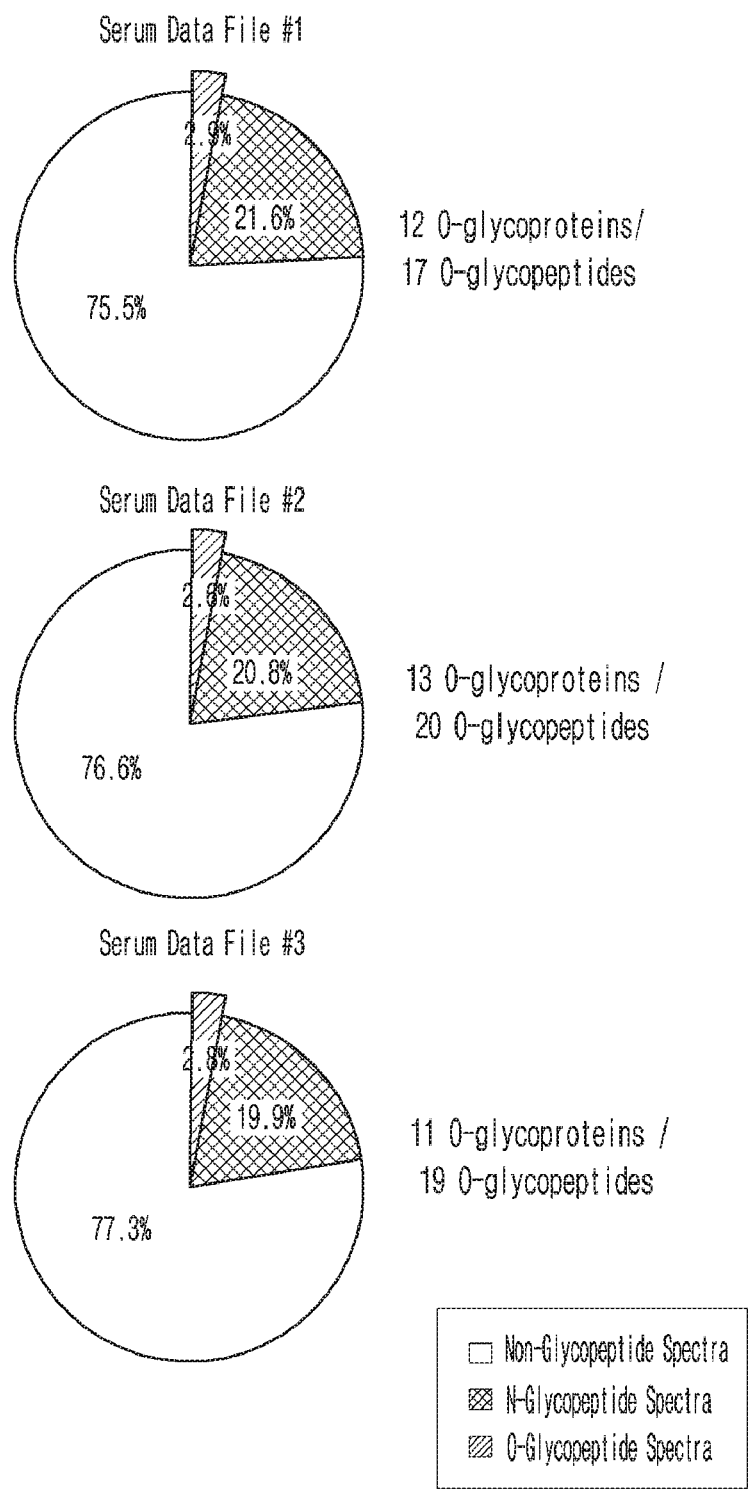
[Figure 10b]

[Figure 11a]
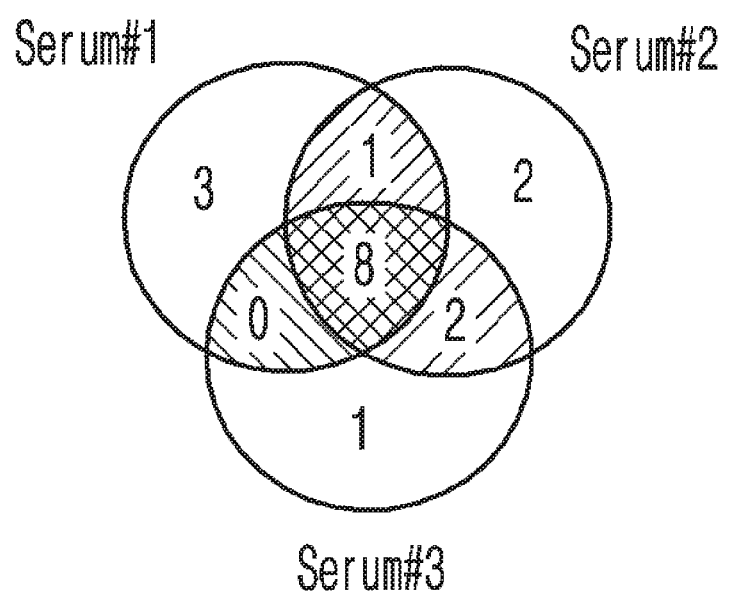

[Figure 11b]
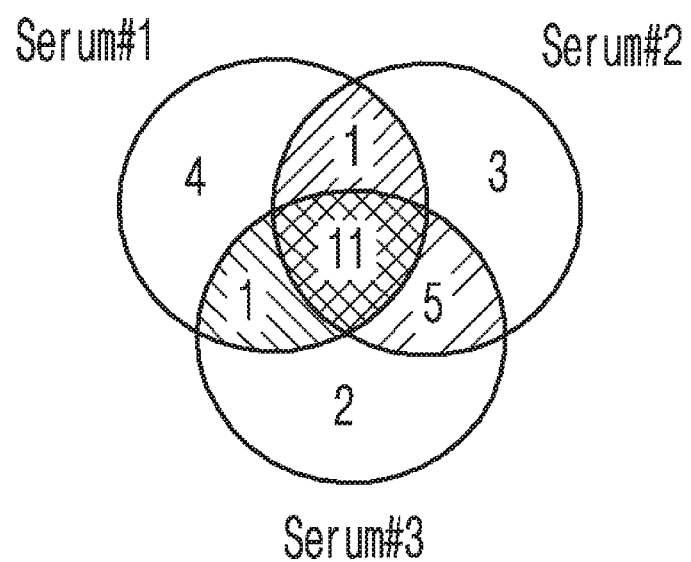

[Figure 12]

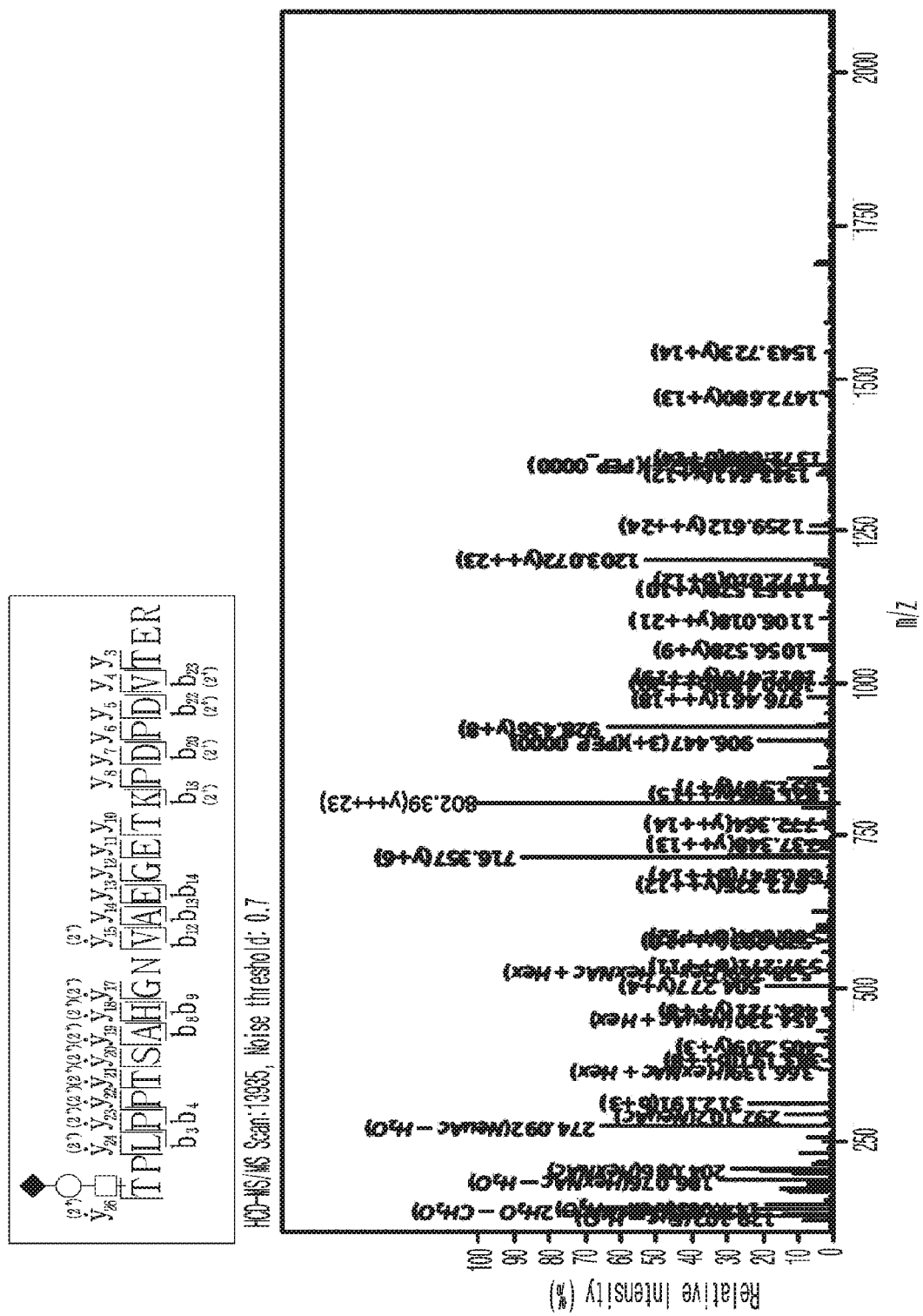
[Figure 13a]

[Figure 13b]
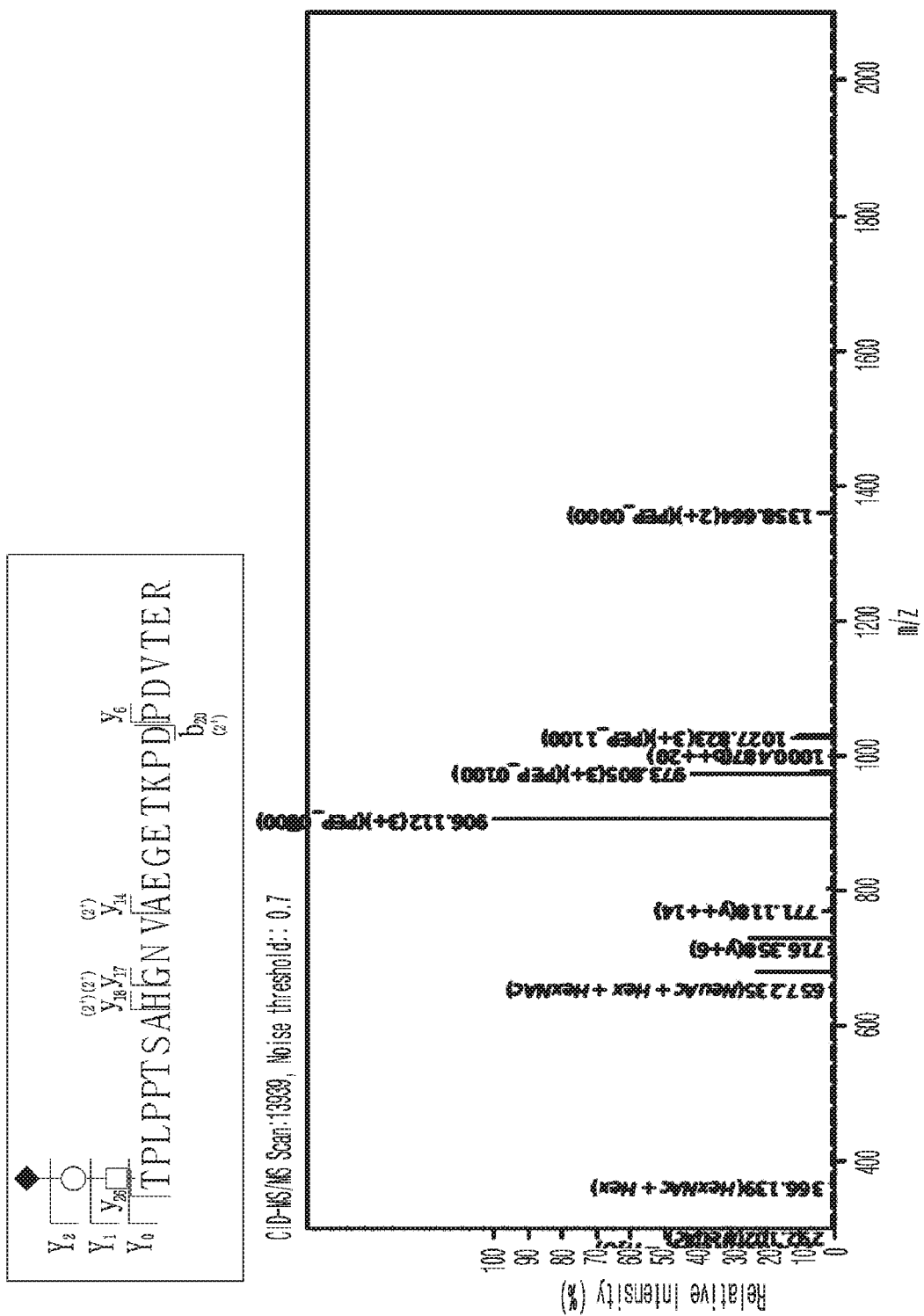

[Figure 13c]
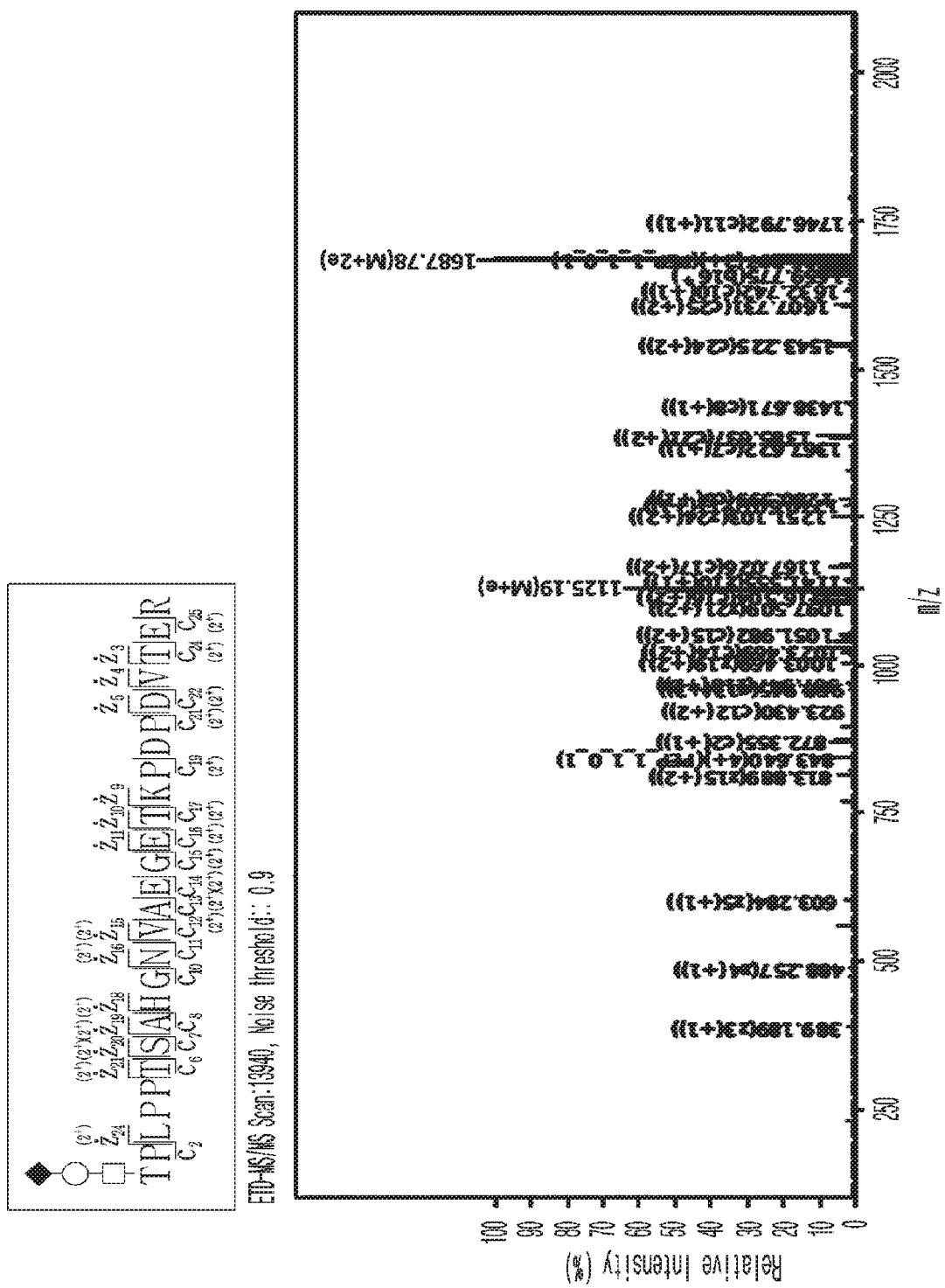

[Figure 13d]
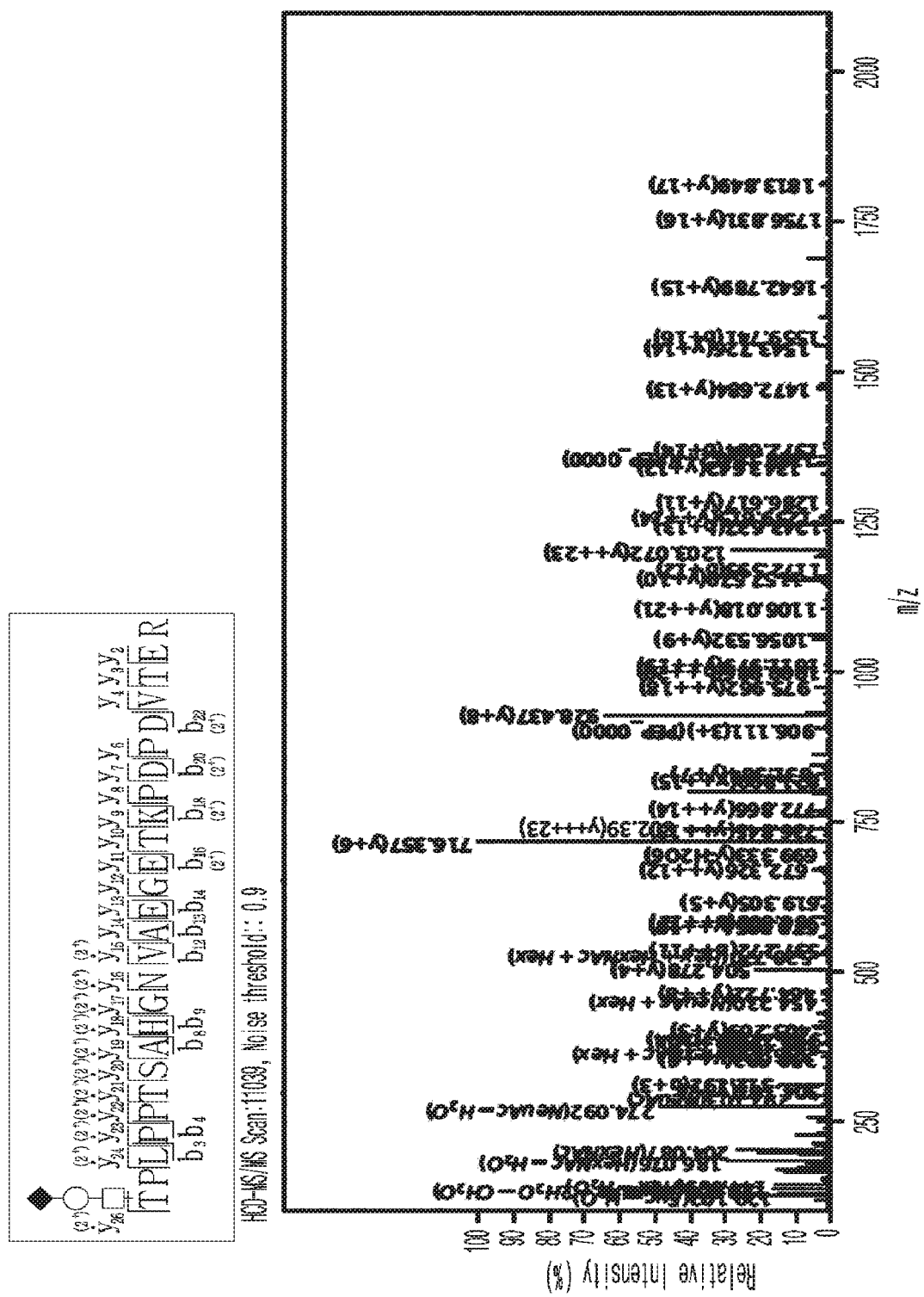

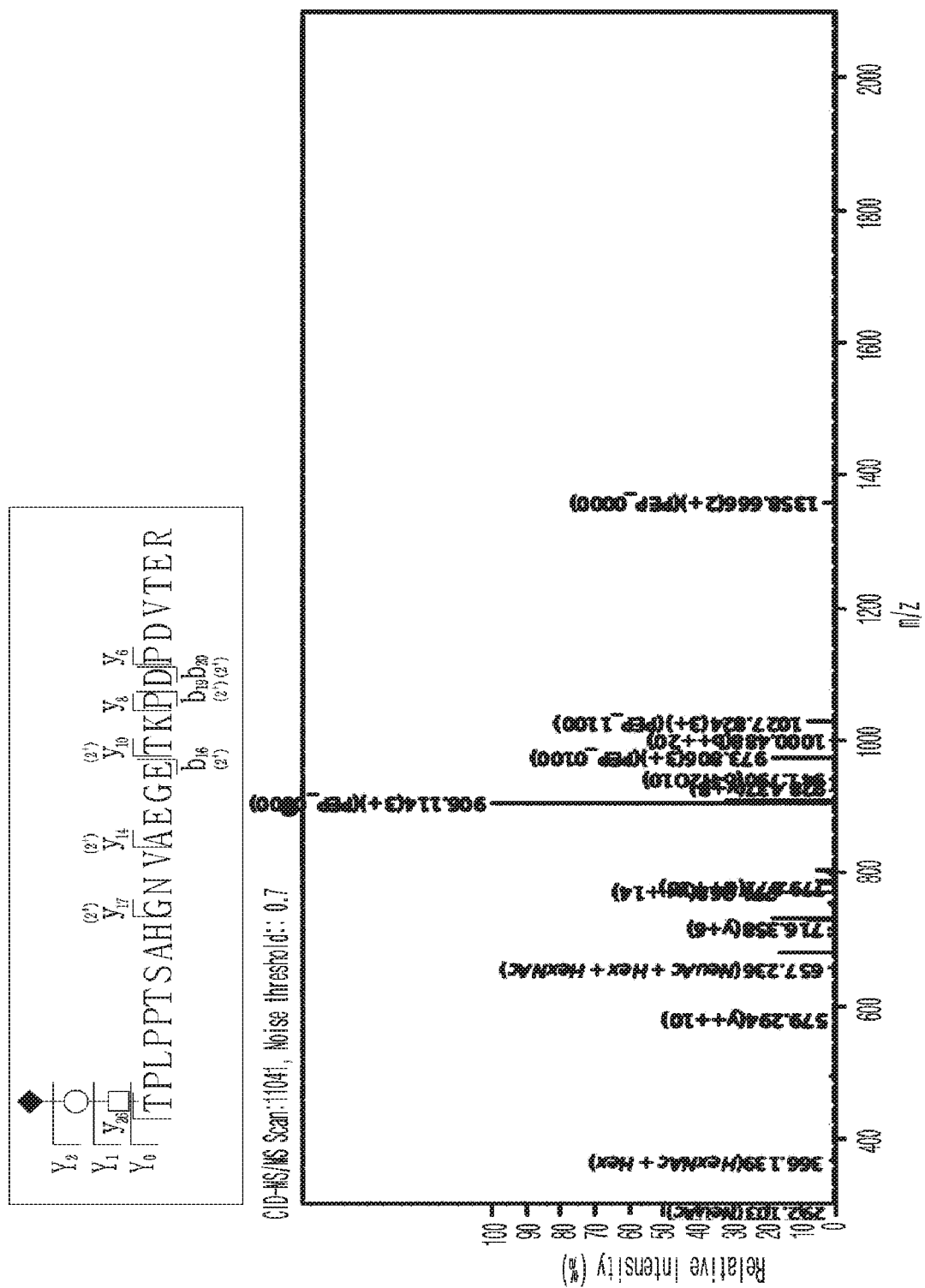
[Figure 13e]

[Figure 13f]
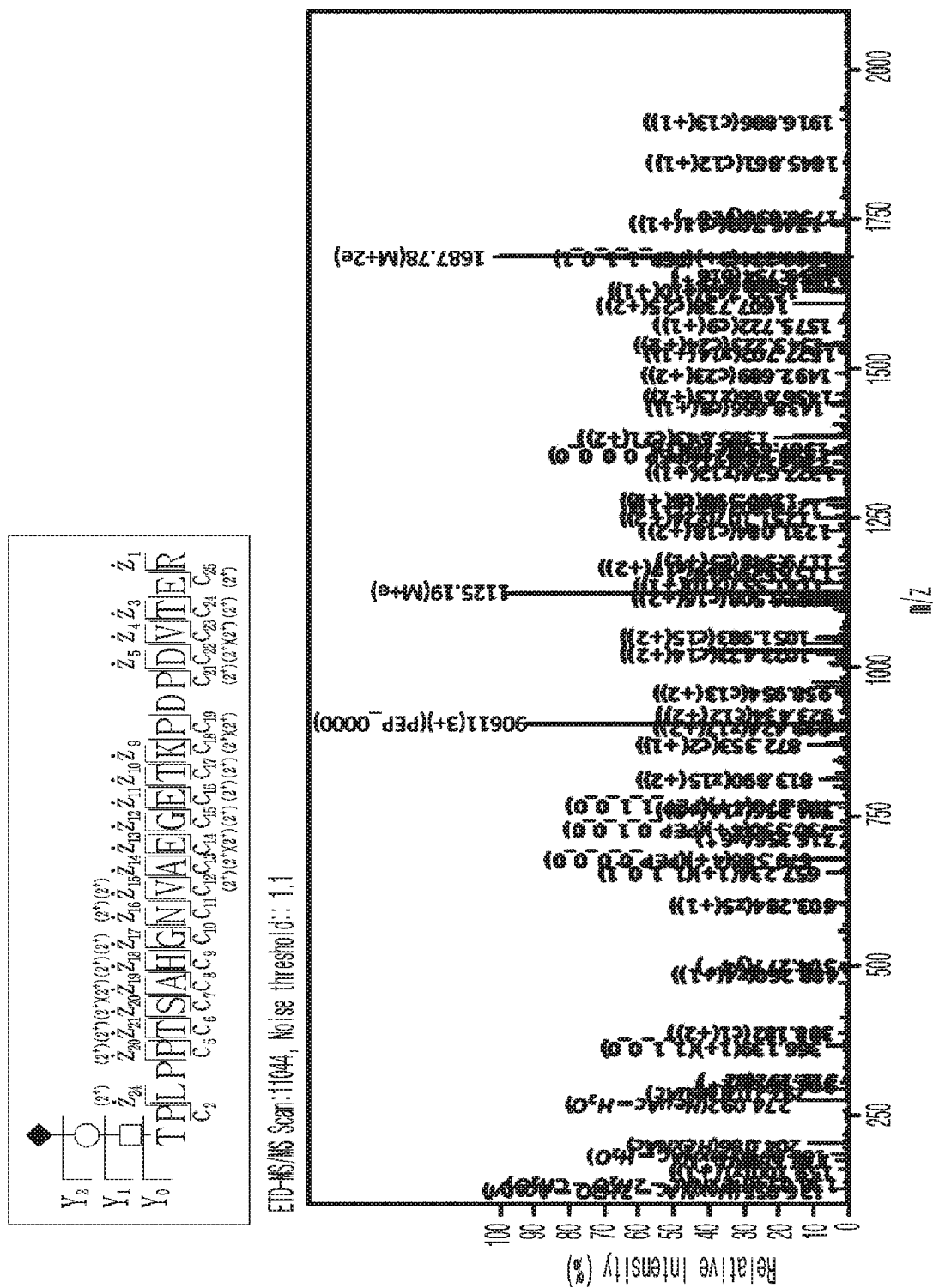

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial
<220> FEATURE:
<223> OTHER INFORMATION: glycosylated with 2HexNAc-2Hex at any amino
      acid
<220> FEATURE:
<221> NAME/KEY: MISC_FEATURE
<222> LOCATION: (1)..(1)
<223> OTHER INFORMATION: glycosylated with 2HexNAc-2Hex at any amino
      acid

<400> SEQUENCE: 1

Thr Pro Leu Pro Pro Thr Ser Ala His Gly Asn Val Ala Glu Gly Glu
1               5                   10                  15

Thr Lys Pro Asp Pro Asp Val Thr Glu Arg
            20                  25

<210> SEQ ID NO 2
<211> LENGTH: 26
<212> TYPE: PRT
<213> ORGANISM: Artificial
<220> FEATURE:
```

-continued

```
<223> OTHER INFORMATION: glycosylated with HexNAc-Hex-Neu5Ac at any
      amino acid
<220> FEATURE:
<221> NAME/KEY: MISC_FEATURE
<222> LOCATION: (1)..(1)
<223> OTHER INFORMATION: glycosylated with HexNAc-Hex-Neu5Ac at any
      amino acid

<400> SEQUENCE: 2

Thr Pro Leu Pro Pro Thr Ser Ala His Gly Asn Val Ala Glu Gly Glu
1               5                   10                  15

Thr Lys Pro Asp Pro Asp Val Thr Glu Arg
            20                  25
```

BIOINFORMATICS PLATFORM FOR HIGH-THROUGHPUT IDENTIFICATION AND QUANTIFICATION OF O-GLYCOPEPTIDE

CROSS-REFERENCE TO RELATED APPLICATIONS

This application is a U.S. National Stage Application filed under 35 U.S.C. § 371 of International Application No. PCT/KR2017/014856, filed Dec. 15, 2017, which claims the benefit of Korean Application No. KR 10-2017-0124401, filed Sep. 26, 2017. Both of these applications are hereby incorporated by reference in their entireties.

BACKGROUND OF THE INVENTION

Field of the Invention

The present invention relates to a bioinformation processing analysis method for the identification and relative quantification of O-linked glycopeptide using high resolution mass spectrum.

Description of the Related Art

Human blood is a mixture of numerous proteins. Among those proteins, at least 50% are glycoproteins. However, it is difficult to perform qualitative analysis or quantitative analysis of glycoproteins compared with other proteomes because of the diversity and complexity of sugars. Recently, the analysis of sugar or glycoprotein has been developed rapidly with the introduction of a high resolution mass spectrometer. However, new techniques in the field of bioinformation processing to identify or quantify glycoprotein based on the results obtained by the method above are still required.

Protein glycosylation is divided into N-linked glycosylation and O-linked glycosylation. N-linked glycosylation occurs in endoplasmic reticulum (ER), while O-linked glycosylation occurs in ER, Golgi apparatus or cytoplasm. O-linked glycosylation is classified into non-mucin type and mucin type. O-linked glycosylation observed mammals is mainly mucin type. Mucin type glycosylation is initiated when N-acetylgalactosamine (GalNAc) binds to serine or threonine. This type of glycosylation is complicated because it is induced by enzymes directly without help of a precursor like dolichol. Mucin type O-linked glycoprotein is mainly observed in cytoplasm or nucleus. Since O-linked glycosylation has not been studied as much as N-linked glycosylation, it is not well known yet.

In total glycoproteins, 12% contain O-linked type, and 10% of them contain both N-linked type and O-linked type. So, it is very difficult to analyze O-linked glycopeptides because they have relatively low sensitivity due to the influence of N-linked glycopeptides and general peptides.

The conventional methods used for the qualitative and quantitative analysis of O-linked glycopeptides have the following limitations. First, while the basic structure of O-linked glycopeptide has been known, the composition of new O-linked glycopeptide has not been clarified because of the diversity of O-linked glycopeptide. Thus, there is a difficulty in creating database for the complete O-linked glycopeptide. Second, mucin type O-linked glycosylation is mainly found in animals, which starts when N-acetylgalactosamine binds to oxygen atom of serine or threonine. However, since serine and threonine are found frequently in the amino acid sequence composing a protein, two or more O-linked glycosylation sites may exist in the O-linked glycopeptide to be analyzed.

There are commercial softwares such as SimGlycan (Arun Apte, Ningombam Sanjib Meitei, et al., Bioinformatics in Glycomics: Glycan Characterization with Mass Spectrometric Data Using SimGlycan™ Springer Protocols, 2009, 269-281) and Byonic (Bern, M. et al., Current Protocols in Bioinformatics; Wiley: New York, 2012, Chapter 13, Unit 13.20) to screen O-linked glycopeptide by using mass spectrum or tandem mass spectrum. As a freeware software, GlycoMID (Yanlin Zhang et al., Identification of Glycopeptides with Multiple Hydroxylysine O-Glycosylation Sites by Tandem Mass Spectrometry, Journal of proteome research, 2015, 14, 5099-5108), SweetNET (Waqas Nasir et al., SweetNET: A Bioinformatics Workflow for Glycopeptide MS/MS Spectral Analysis, Journal of proteome research, 2016, 15, 2826-2840), GPQuest (Shadi Toghi Eshghi et al., Classification of Tandem Mass Spectra for Identification of N- and O-linked glycopeptides, Scientific Reports, 2016, DOI: 10.1038/srep37189), GlycResoft (Evan Maxwell et al., GlycResoft: A Software Package for Automated Recognition of Glycans from LC/MS Data, PLOS one, 2012.7.9. e45474), and Protein Prospector (Robert J. Chalkley et al., Use of a glycosylation site database to improve glycopeptide identification from complex mixtures, Analytical and Bioanalytical Chemistry, 2017, 409, 2, pp. 571-577) have been developed as an academic version and used.

However, the programs above could only screen such sugar chain sites or sugar chain structures that exist in database, suggesting that new sugar chains that are not present in the O-linked glycopeptide database cannot be identified. Moreover, the programs above do not allow qualitative and quantitative analysis simultaneously and do not provide various fragmentation spectra of a high resolution mass spectrometer.

Thus, the present inventors studied and finally established an analysis method that can overcome the problems above and achieve the identification and quantitative analysis of O-linked glycopeptide having a relatively low sensitivity (or concentration), compared with a general peptide or N-linked glycopeptide, efficiently and accurately. Particularly, 11 kinds of well-known O-linked sugar chain structures (Essentials of Glycobiology, Second Edition: 1) HexNAc, 2) HexNAc-Neu5Ac, 3) 2HexNAc, 4) 2HexNAc-Neu5Ac, 5) 3HexNAc, 6) HexNAc-Hex, 7) HexNAc-Hex-Neu5Ac, 8) HexNAc-Hex-2Neu5Ac, 9) 2HexNAc-Hex, 10) 2HexNAc-2Hex, 11) 3HexNAc-1Hex) and O-linked sugar chain sites informed to Uniprot database were all stored in the database of the invention, followed by modeling the distribution of theoretical isotopes of the stored O-linked glycopeptides, resulting in the construction of the database. In the meantime, O-linked glycopeptide was accurately identified regardless of sugar chain sites or structures by comparing the distribution of isotopes of the glycopeptides obtained by tandem mass spectrum (MS/MS) or mass spectrum (MS) with the database above or by using new O-family search method. Thereafter the present inventors confirmed that the quantitative analysis was successfully accomplished without any additional labeling process by calculating TIQ (top three isotope quantitation) using ion chromatograms, leading to the completion of the present invention.

SUMMARY OF THE INVENTION

It is an object of the present invention to provide a bioinformation processing analysis method to achieve the identification and quantitative analysis of O-linked glycopeptide having a relatively low sensitivity (or concentration) compared with a general peptide from the results of mass spectrometry, efficiently and accurately.

To achieve the object above, the present invention provides a bioinformation processing analysis method for the identification and quantification of O-linked glycopeptide comprising the following steps: 1) obtaining mass spectrum by analyzing the polypeptide obtained by hydrolyzing the glycoprotein in a sample with a high resolution mass spectrometer; 2) converting the mass spectrum results obtained in step 1) into MS and tandem spectrum (MS/MS); 3) calculating M-score of each tandem spectrum by using oxonium ion peaks composed of m/z of the HCD-MS/MS individual spectrum peak converted in step 2) of 126.05, 129.06, 138.06, 144.06, 145.05, 147.07, 163.06, 168.07, 186.08, 204.08, 274.09, 292.10, 350.15, 366.14, 454.16, 528.19, and 657.24; 4) determining a value for separating the glycopeptide and the peptide using Gaussian fitting method in the M-score distribution calculated in step 3), and selecting the glycopeptide spectrum; 5) selecting O-linked glycopeptide spectrum by using O-linked and N-linked sorting factors (O/N sorting factors) from the glycopeptide spectrum selected in step 4); 6) obtaining the isotope distribution in MS of the O-linked glycopeptide spectrum selected in step 5) and then determining the O-linked glycopeptide existing in the database using S-score calculated by comparing with the database; 7) evaluating the O-linked glycopeptide existing in the database determined in step 6) by using Y-score of the tandem spectrum; 8) determining O-linked sugar site by calculating P-score for the O-linked glycopeptide existing in the database evaluated in step 7) and then performing quantitative analysis of the O-linked glycopeptide included in the database evaluated above; 9) selecting the O-linked glycopeptide that does not exist in the database by using O-family search method based on the O-linked glycopeptide existing in the database quantitatively analyzed (root/seed) in step 8); 10) evaluating the O-linked glycopeptide that does not exist in the database by using Y-score of the tandem spectrum obtained from the O-linked glycopeptide confirmed not to exist in the database selected in step 9); and 11) determining O-linked sugar site by calculating P-score for the O-linked glycopeptide that does not exist in the database evaluated in step 10) and then performing quantitative analysis of the O-linked glycopeptide that does not exist in the database evaluated above.

Advantageous Effect

The bioinformation processing analysis method according to the present invention facilitates efficient and accurate analysis of the quantitative changes of O-linked glycopeptide having non-informed sugar chains included in various samples and can be used for the prediction or diagnosis of disease including cancer by identifying a disease marker or for the analysis of O-linked glycopeptide structure of a therapeutic glycoprotein using a high resolution mass spectrometer.

BRIEF DESCRIPTION OF THE DRAWINGS

The application of the preferred embodiments of the present invention is best understood with reference to the accompanying drawings, wherein:

FIG. 1 is a flowchart illustrating the bioinformation processing analysis method for the identification and quantification of O-linked glycopeptide according to the present invention.

FIG. 2 is a diagram illustrating the M-score distribution of a general peptide and a glycopeptide obtained in step 3) of the bioinformation processing analysis method for the identification and quantification of O-linked glycopeptide of the present invention using a standard glycoprotein.

FIG. 3 is a diagram illustrating the classification of O-linked and N-linked peptides from the glycopeptides selected in step 4) by using O-linked and N-linked sorting factors in step 5) of the bioinformation processing analysis method for the identification and quantification of O-linked glycopeptide of the present invention using a standard glycoprotein.

FIG. 4 is a diagram illustrating the Y-score distribution in step 7) of the bioinformation processing analysis method for the identification and quantification of O-linked glycopeptide of the present invention using a standard glycoprotein.

FIG. 5 is a diagram illustrating the O-family search method in step 10) of the bioinformation processing analysis method for the identification and quantification of O-linked glycopeptide of the present invention using a standard glycoprotein.

FIGS. 6a and 6b are diagrams illustrating that the spectrum similarity in the O-family search method in step 10) of the bioinformation processing analysis method for the identification and quantification of O-linked glycopeptide of the present invention using a standard glycoprotein is 0.97.

FIG. 7 is a diagram illustrating the Y-score distribution in step 11) of the bioinformation processing analysis method for the identification and quantification of O-linked glycopeptide of the present invention using a standard glycoprotein.

FIGS. 8a and 8b are diagrams illustrating the representative EThcD spectrum of T(HexNAc-Hex)PLPPT(HexNAc-Hex) SAHGNVAEGETK PDPDVTER, the O-linked glycopeptide, selected by the bioinformation processing analysis method for the identification and quantification of O-linked glycopeptide of the present invention using a standard glycoprotein.

FIGS. 9a and 9b are diagrams illustrating the representative EThcD spectrum of T(2HexNAc-2Hex)PLPPT-SAHGNVAEGETKPDPDVTER, the O-linked glycopeptide, selected by the bioinformation processing analysis method for the identification and quantification of O-linked glycopeptide of the present invention using a standard glycoprotein.

FIG. 10a is a diagram illustrating the results of the bioinformation processing analysis for the identification and quantification of O-linked glycopeptide of the present invention repeated three times by using human serum samples in a preferred embodiment of the invention.

FIG. 10b is a graph illustrating the results of the bioinformation processing analysis for the identification and quantification of O-linked glycopeptide of the present invention repeated three times by using human serum samples in a preferred embodiment of the invention.

FIG. 11a is a Venn diagram illustrating the results of qualitative analysis of glycoprotein according to the bioinformation processing analysis method for the identification and quantification of O-linked glycopeptide of the present invention using human serum samples in a preferred embodiment of the invention.

FIG. 11b is a Venn diagram illustrating the results of qualitative analysis of O-linked glycopeptide according to the bioinformation processing analysis method for the identification and quantification of O-linked glycopeptide of the present invention using human serum samples in a preferred embodiment of the invention.

FIG. 12 is a diagram illustrating the heat map showing the results of quantitative analysis of O-linked glycopeptide according to the bioinformation processing analysis method for the identification and quantification of O-linked glycopeptide of the present invention using human serum samples in a preferred embodiment of the invention.

FIG. 13a is a diagram illustrating the representative HCD (high energy collision dissociation) spectrum of TPLPPT-SAHGNVAEGETKPDPDVTER(HexNAc-Hex-Neu5Ac) (SEQ. ID. NO: 2), the O-linked glycopeptide selected based on the results of the bioinformation processing analysis for the identification and quantification of O-linked glycopeptide of the present invention using human serum samples in a preferred embodiment of the invention.

FIG. 13b is a diagram illustrating the representative CID (collision-induced dissociation) spectrum of TPLPPT-SAHGNVAEGETKPDPDVTER (HexNAc-Hex-Neu5Ac) (SEQ. ID. NO: 2), the O-linked glycopeptide selected based on the results of the bioinformation processing analysis for the identification and quantification of O-linked glycopeptide of the present invention using human serum samples in a preferred embodiment of the invention.

FIG. 13c is a diagram illustrating the representative ETD (electron transfer dissociation) spectrum of TPLPPT-SAHGNVAEGETKPDPDVTER (HexNAc-Hex-Neu5Ac) (SEQ. ID. NO: 2), the O-linked glycopeptide selected based on the results of the bioinformation processing analysis for the identification and quantification of O-linked glycopeptide of the present invention using human serum samples in a preferred embodiment of the invention.

FIG. 13d is a diagram illustrating the representative HCD spectrum of T(HexNAc-Hex-Neu5Ac)PLPPTSAHGNVAE-GETKPDPDVTER, the O-linked glycopeptide selected based on the results of the bioinformation processing analysis for the identification and quantification of O-linked glycopeptide of the present invention using a standard glycoprotein in a preferred embodiment of the invention.

FIG. 13e is a diagram illustrating the representative CID spectrum of T(HexNAc-Hex-Neu5Ac)PLPPTSAHGNVAE-GETKPDPDVTER, the O-linked glycopeptide selected based on the results of the bioinformation processing analysis for the identification and quantification of O-linked glycopeptide of the present invention using a standard glycoprotein in a preferred embodiment of the invention.

FIG. 13f is a diagram illustrating the representative EThcD (electron-transfer/higher-energy collision dissociation) of T(HexNAc-Hex-Neu5Ac)PLPPTSAHGNVAE-GETKPDPDVTER, the O-linked glycopeptide selected based on the results of the bioinformation processing analysis for the identification and quantification of O-linked glycopeptide of the present invention using a standard glycoprotein in a preferred embodiment of the invention.

DESCRIPTION OF THE PREFERRED EMBODIMENTS

Hereinafter, the present invention is described in detail.

The present invention provides a bioinformation processing analysis method for the identification and quantification of O-linked glycopeptide comprising the following steps: 1) obtaining mass spectrum by analyzing the polypeptide obtained by hydrolyzing the glycoprotein in a sample with a high resolution mass spectrometer; 2) converting the mass spectrum results obtained in step 1) into MS and tandem spectrum (MS/MS); 3) calculating M-score of each tandem spectrum by using oxonium ion peaks composed of m/z of the HCD-MS/MS individual spectrum peak converted in step 2) of 126.05, 129.06, 138.06, 144.06, 145.05, 147.07, 163.06, 168.07, 186.08, 204.08, 274.09, 292.10, 350.15, 366.14, 454.16, 528.19, and 657.24; 4) determining a value for separating the glycopeptide and the peptide using Gaussian fitting method in the M-score distribution calculated in step 3), and selecting the glycopeptide spectrum; 5) selecting O-linked glycopeptide spectrum by using O-linked and N-linked sorting factors (O/N sorting factors) from the glycopeptide spectrum selected in step 4); 6) obtaining the isotope distribution in MS of the O-linked glycopeptide spectrum selected in step 5) and then determining the O-linked glycopeptide existing in the database using S-score calculated by comparing with the database; 7) evaluating the O-linked glycopeptide existing in the database determined in step 6) by using Y-score of the tandem spectrum; 8) determining O-linked sugar site by calculating P-score for the O-linked glycopeptide existing in the database evaluated in step 7) and then performing quantitative analysis of the O-linked glycopeptide included in the database evaluated above; 9) selecting the O-linked glycopeptide that does not exist in the database by using O-family search method based on the O-linked glycopeptide existing in the database quantitatively analyzed (root/seed) in step 8); 10) evaluating the O-linked glycopeptide that does not exist in the database by using Y-score of the tandem spectrum obtained from the O-linked glycopeptide confirmed not to exist in the database selected in step 9); and 11) determining O-linked sugar site by calculating P-score for the O-linked glycopeptide that does not exist in the database evaluated in step 10) and then performing quantitative analysis of the O-linked glycopeptide that does not exist in the database evaluated above.

The term "hydrolysis" used herein refers the process of separating only sugars from glycoproteins. The hydrolysis herein can be performed by any method which is well known to those in the art. In particular, the hydrolysis can be performed with a hydrolase which is precisely selected from the group consisting of trypsin, arginine-C (Arg-C), aspartic acid-N (Asp-N), glutamic acid-C (Glu-C), lysine-C (Lys-C), chymotrypsin, and proteinase K.

The term "tandem spectrum (MS/MS)" used herein refers the spectrum of the target ions of interest or the ions having a relatively high sensitivity selected among total mass spectrum (MS). The tandem mass analysis can be performed by analyzing the mass of the tandem spectrum. Based on the O-linked glycopeptides present in the database determined by the tandem spectrum (root/seed), such O-linked glycopeptides that do not exist in the database can be screened by performing O-family search method. The tandem spectrum above can be CID or HCD-MS/MS spectrum.

According to the analysis method of the invention, a mass spectrometer can be used to perform qualitative and quantitative analysis of O-linked glycopeptides which are more complicated than general peptides and have high diversity and are present in a low concentration in a sample. From the results obtained by using the mass spectrometer, O-linked glycopeptide can be identified using M-score, S-score, Y-score, and P-score and quantitative analysis of the identified glycopeptide can be performed. The mass spectrometer may have a mass resolution of more than 10,000 and a mass accuracy of less than 50 ppm. Particularly, the mass spectrometer herein can be Orbitrap Fusion Lumos, Orbitrap Elite, or Q Exactive.

The M-score above is used to classify the general peptide spectrum and the glycopeptide spectrum efficiently. The M-score can be calculated by mathematical formula 1 below:

[Mathematical Formula 1]

$$M_{score} = \frac{n}{N} \times \frac{\sqrt{\sum_{i=1}^{n} O_i}}{(n-1)}, \text{ where } O_i = \frac{I_{mi} \times I_{max(\leq 700Da)}^{-1} \times C}{|MassError| + 1.0}$$

(N is the number of confirmable sugar peaks,
n is the number of confirmed sugar peaks,
$I_{mi}$ is the matched $i^{th}$ peak intensity,
$I_{max}$ is the intensity of the base peak in the spectrum, and
C is a constant value).

M-score distribution map can be prepared from the HCD-MS/MS spectra of the glycoprotein standard sample (hemopexin) according to the method above (FIG. 2). The distribution map can be used to classify general peptides and glycopeptides by automatically applying Gaussian fitting.

In step 5) of the analysis method of the present invention, the O-linked glycopeptide spectrum showing O/N sorting factor of up to 4.0 can be determined from the glycopeptides spectrum selected by using the M-score distribution map prepared in step 4) (FIG. 3). At this time, the O/N sorting factor can be calculated by mathematical formula 5 below:

O/NSorting Factor=$O_{i(138)}+O_{i(168)}/O_{i(126)}+I_{i(144)}$      [Mathematical Formula 5]

In the analysis method of the present invention, S-score is used to identify glycopeotides by comparing the theoretical database with the isotope distribution obtained by MS of the glycopeptides spectrum in step 6). This value can be calculated by mathematical formula 2 below:

[Mathematical Formula 2]

$$S_{score} = \left(\frac{1.0}{\left(1.0 + \sum_{i=1}^{n}(X1-Y1)_i^2\right)} * C1\right) + \left(\frac{n(\sum X2Y2) - (\sum X2)(\sum Y2)}{\sqrt{(n\sum X2^2 - (\sum X2)^2) * (n\sum Y2^2 - (\sum Y2)^2)}} * C2\right)$$

(X1 is the mass of the $n^{th}$ peak among the theoretical isotope peaks,
Y1 is the mass of the $n^{th}$ peak among the experimental isotope peaks,
X2 is the relative intensity of the $n^{th}$ peak among the theoretical isotope peaks,
Y2 is the relative intensity of the $n^{th}$ peak among the experimental isotope peaks,
C1 and C2 are constant values).

When the S-score is calculated, the similarity can be measured using Pearson correlation analysis with the Euclidean distance and the intensity distribution using the mass distribution of isotopes. In step 6), a database was constructed by using the theoretical isotope distribution of the glycopeptide obtained from glycoproteins. Then, the database can be used for the identification and quantitative analysis of O-linked glycopeptide. The term "isotope" used herein refers a chemical element that has the same atomic number but has the different atomic mass.

In the analysis method of the present invention, the degree of glycopeptide fragmentation, which can theoretically be expressed using O-family search method, of the O-linked glycopeptide candidate or the O-linked glycopeptides (FIG. 4) evaluated using Y-score in steps 7) and 10) can be calculated and evaluated by the Y-score in tandem spectrum (CID or HCD) (FIGS. 8 and 9). At this time, the Y-score can be calculated by mathematical formula 3 below, which can be expressed by the sum of $HCD_{match}$ and $CID_{match}$:

[Mathematical Formula 3]

$$Y_{score} = HCD_{match} \times C1 + CID_{match} C2$$

$$HCD_{match} = \sum_{i=1}^{n} \frac{I_{mi}}{I_{max}} \Big/ \sum_{i=1}^{n} \frac{I_{si}}{I_{max}} \times 100.0$$

$$CID_{match} = \sum_{i=1}^{n} \frac{I_{mi}}{I_{max}} \Big/ \sum_{i=1}^{n} \frac{I_{si}}{I_{max}} \times 100.0$$

($I_{max}$ is the intensity of the base peak in the spectrum,
$I_{mi}$ is the matched $i^{th}$ peak intensity,
$I_{si}$ is the $i^{th}$ peak intensity, and
C1 and C2 are constant values).

In the analysis method of the present invention, the P-score in step 8) or step 11) is used to confirm and evaluate the degree of glycopeptide fragmentation, which can theoretically be expressed, in tandem spectrum (ETD/EThcD). The P-score above can be used to specify the glycosylated site position, which can be calculated by mathematical formula 4 below:

$$P_{score} = \frac{n}{N} \times \sum_{i=1}^{n} \frac{I_{mi}}{I_{max}}$$      [Mathematical Formula 4]

(N is the number of peptide fragments (c, z ion) of the confirmable glycopeptide,
n is the number of peptide fragments of the confirmed glycopeptide,
$I_{max}$ is the intensity of the base peak in the spectrum, and
$I_{mi}$ is the matched $i^{th}$ peak intensity).

In the method above, the quantitative analysis in step 8) or step 11) can be performed by using S-score in MS spectra. This can be expressed by summing the intensities of the three peaks from the theoretical maximum intensity among the isotope peaks showing the intensity of the selected glycopeptide in MS spectra.

In the analysis method of the present invention, O-linked glycopeptides that are not present in the database can be selected by using O-family search method based on the O-linked glycopeptides (root/seed) present in the database determined using the tandem spectrum of step 9) (FIG. 5). At this time, the selection can be calculated by mathematical formula 6 below. The spectral similarity (SS) can be used to find similar spectra and the value may be greater than or equal to 0.9 (FIG. 6):

$$SS = \frac{\sum_{i=1}^{n} S_i \times S_i'}{\sqrt{\sum_{i=1}^{n} S_i^2 \times \sum_{i=1}^{n} S_i'^2}}$$      [Mathematical Formula 6]

(SS: two different tandem mass spectrometry spectrum peaks and mass similarity,

Si: (x, y) matrix, x is the relative intensity of the $n^{th}$ peak, y is the mass of the $n^{th}$ peak, and S'i: (x', y') matrix, x' is the relative intensity of the $n^{th}$ peak n, y' is the mass of the $n^{th}$ peak).

The present inventors present the results of the analysis up to step 8) performed by using the HCD, CID, and EThcD (electron-transfer/higher-energy collision dissociation) spectrum obtained from glycopeptide of the standard glycoprotein sample (hemopexin) using Orbitrap, the high resolution mass spectrometer, before O-family searching in Table 1 below (Table 1).

TABLE 1

| O-Glycopeptides | Charge | m/z | MS/MS RT | MS scan | HCD-MS/ M scan | O/N S. Factor |
|---|---|---|---|---|---|---|
| TPLPPTSAHGNVAEGETKPDPDVTER_(HexNAc) | 3 | 973.473 | 38.8 | 8993 | 8994 | 1.6 |
| TPLPPTSAHGNVAEGETKPDPDVTER_(HexNAc) | 4 | 730.357 | 35.7 | 7487 | 7488 | 2.0 |
| TPLPPTSAHGNVAEGETKPDPDVTER_(HexNAc-Neu5Ac) | 3 | 1070.505 | 42.4 | 10672 | 10674 | 2.1 |
| TPLPPTSAHGNVAEGETKPDPDVTER_(HexNAcNeu5Ac) | 4 | 803.131 | 42.5 | 10737 | 10756 | 1.4 |
| TPLPPTSAHGNVAEGETKPDPDVTER_(HexNAc-Hex) | 3 | 1027.490 | 39.5 | 9299 | 9303 | 2.2 |
| TPLPPTSAHGNVAEGETKPDPDVTER_(HexNAc-Hex) | 4 | 770.870 | 39.1 | 9118 | 9128 | 2.1 |
| TPLPPTSAHGNVAEGETKPDPDVTER_(HexNAc-Hex-Neu5Ac) | 3 | 1124.521 | 43.3 | 11137 | 11138 | 2.3 |
| TPLPPTSAHGNVAEGETKPDPDVTER_(HexNAc-Hex-Neu5Ac) | 4 | 843.644 | 43.1 | 11038 | 11039 | 2.0 |
| TPLPPTSAHGNVAEGETKPDPDVTER_(HexNAc-2Neu5Ac) | 3 | 1221.553 | 42.9 | 10935 | 10955 | 1.7 |
| TPLPPTSAHGNVAEGETKPDPDVTER_(HexNAc-2Neu5Ac) | 4 | 916.419 | 47.9 | 13119 | 13133 | 2.0 |
| TPLPPTSAHGNVAEGETKPDPDVTER_(2HexNAc-Hex) | 4 | 821.643 | 33.6 | 6484 | 6486 | 2.3 |
| TPLPPTSAHGNVAEGETKPDPDVTER_(2HexNAc-2Hex) | 3 | 1149.201 | 34.1 | 6703 | 6704 | 2.2 |
| TPLPPTSAHGNVAEGETKPDPDVTER_(2HexNAc-2Hex) | 4 | 862.149 | 36.8 | 8011 | 8027 | 2.3 |

| O-Glycopeptides | M-score | S-score | Y-score | MS RT | Three TIQ |
|---|---|---|---|---|---|
| TPLPPTSAHGNVAEGETKPDPDVTER_(HexNAc) | 1.6 | 99.8 | 79.8 | 38.5 | 231629754 |
| TPLPPTSAHGNVAEGETKPDPDVTER_(HexNAc) | 2.0 | 100.0 | 75.8 | 38.4 | 114832679 |
| TPLPPTSAHGNVAEGETKPDPDVTER_(HexNAc-Neu5Ac) | 2.1 | 98.0 | 73.8 | 42.6 | 3196957 |
| TPLPPTSAHGNVAEGETKPDPDVTER_(HexNAcNeu5Ac) | 1.4 | 99.6 | 74.3 | 42.5 | 3821353 |
| TPLPPTSAHGNVAEGETKPDPDVTER_(HexNAc-Hex) | 2.2 | 98.6 | 85.2 | 35.3 | 192574557 |
| TPLPPTSAHGNVAEGETKPDPDVTER_(HexNAc-Hex) | 2.1 | 98.7 | 75.4 | 35.3 | 2437221120 |
| TPLPPTSAHGNVAEGETKPDPDVTER_(HexNAc-Hex-Neu5Ac) | 2.3 | 98.7 | 84.1 | 38.5 | 2198194752 |
| TPLPPTSAHGNVAEGETKPDPDVTER_(HexNAc-Hex-Neu5Ac) | 2.0 | 99.8 | 76.2 | 38.5 | 15466424704 |
| TPLPPTSAHGNVAEGETKPDPDVTER_(HexNAc-2Neu5Ac) | 1.7 | 99.8 | 82.6 | 42.6 | 118725937 |
| TPLPPTSAHGNVAEGETKPDPDVTER_(HexNAc-2Neu5Ac) | 2.0 | 99.8 | 75.8 | 42.6 | 1600530448 |
| TPLPPTSAHGNVAEGETKPDPDVTER_(2HexNAc-Hex) | 2.3 | 99.7 | 74.4 | 33.8 | 5601061 |
| TPLPPTSAHGNVAEGETKPDPDVTER_(2HexNAc-2Hex) | 2.2 | 99.9 | 84.9 | 33.8 | 27053351 |
| TPLPPTSAHGNVAEGETKPDPDVTER_(2HexNAc-2Hex) | 2.3 | 98.6 | 76.4 | 33.8 | 431081292 |

Herein, the quantitative analysis of O-linked glycopeptides existing in the database qualitatively analyzed using the Y-score distribution map of hemopexin, the standard glycoprotein sample, was performed. At this time, the quantitative analysis was accomplished by summing the three-point TIQ values of each glycopeptide ion chromatogram. The data point to calculate TIQ was the sum of the peak intensities of three isotopes based on the strongest peak.

In the method of the present invention, O-linked glycopeptides that are not present in the database were selected by using O-family search method of step 9) (FIGS. 5 and 6). The O-linked glycopeptides that are not present in the database selected above proceeded to the identification and quantification by using Y-score distribution by the same manner as described above. The results are shown in Table 2 (Table 2).

TABLE 2

| O-Glycopeptides | Charge | m/z | MS/MS RT | MS scan | HCD-MS/ MS scan | O/N S. Factor |
|---|---|---|---|---|---|---|
| TPLPPTSAHGNVAEGETKPDPDVTER_(HexNAc) | 3 | 973.472 | 39.4 | 9255 | 9256 | 0.6 |
| TPLPPTSAHGNVAEGETKPDPDVTER_(HexNAc-Hex) | 3 | 1027.491 | 38.8 | 9007 | 9009 | 0.7 |
| TPLPPTSAHGNVAEGETKPDPDVTER_(HexNAc-Hex) | 4 | 770.870 | 43.6 | 11262 | 11264 | 0.6 |
| TPLPPTSAHGNVAEGETKPDPDVTER_(HexNAc-Hex-Neu5Ac) | 3 | 1124.522 | 36.8 | 8011 | 8028 | 1.6 |
| TPLPPTSAHGNVAEGETKPDPDVTER_(HexNAc-Hex-Neu5Ac) | 4 | 843.643 | 37.4 | 8295 | 8316 | 0.8 |
| TPLPPTSAHGNVAEGETKPDPDVTER_(2HexNAc-2Hex) | 3 | 1149.202 | 34.7 | 6983 | 6998 | 1.8 |
| TPLPPTSAHGNVAEGETKPDPDVTER_(2HexNAc-2Hex) | 4 | 862.153 | 37.0 | 8127 | 8129 | 0.5 |
| TPLPPTSAHGNVAEGETKPDPDVTER_(2HexNAc-2Hex-2Fuc-Neu5Ac) | 4 | 1007.948 | 43.2 | 11083 | 11096 | 0.7 |
| TPLPPTSAHGNVAEGETKPDPDVTER_(2HexNAc-2Hex-2Neu5Ac) | 3 | 1343.264 | 41.9 | 10457 | 10469 | 0.9 |
| TPLPPTSAHGNVAEGETKPDPDVTER_(2HexNAc-2Hex-2Neu5Ac) | 4 | 1007.704 | 41.5 | 10272 | 10292 | 0.6 |

TABLE 2-continued

| | | | | | | |
|---|---|---|---|---|---|---|
| TPLPPTSAHGNVAEGETKPDPDVTER_(2HexNAc-2Hex-2Neu5Ac) | 5 | 806.362 | 40.5 | 9764 | 9778 | 0.6 |
| TPLPPTSAHGNVAEGETKPDPDVTER_(2HexNAc-2Hex-3Neu5Ac) | 4 | 1080.476 | 45.4 | 12123 | 12124 | 0.7 |
| TPLPPTSAHGNVAEGETKPDPDVTER_(2HexNAc-2Hex-3Neu5Ac) | 5 | 864.582 | 43.5 | 11212 | 11229 | 0.7 |
| TPLPPTSAHGNVAEGETKPDPDVTER_(2HexNAc-2Hex-4Neu5Ac) | 4 | 1153.250 | 48.9 | 13435 | 13437 | 1.6 |
| TPLPPTSAHGNVAEGETKPDPDVTER_(2HexNAc-2Hex-4Neu5Ac) | 5 | 922.801 | 47.5 | 12983 | 12987 | 0.9 |
| TPLPPTSAHGNVAEGETKPDPDVTER_(2HexNAc-2Hex-Neu5Ac) | 3 | 1246.232 | 38.0 | 8616 | 8619 | 1.7 |
| TPLPPTSAHGNVAEGETKPDPDVTER_(2HexNAc-2Hex-Neu5Ac) | 4 | 934.927 | 37.9 | 8589 | 8590 | 1.1 |
| TPLPPTSAHGNVAEGETKPDPDVTER_(2HexNAc-2Hex-Neu5Ac) | 5 | 748.144 | 37.3 | 8250 | 8252 | 0.7 |
| TPLPPTSAHGNVAEGETKPDPDVTER_(2HexNAc-Hex-2Neu5Ac) | 4 | 967.186 | 44.3 | 11591 | 11599 | 0.6 |
| TPLPPTSAHGNVAEGETKPDPDVTER_(2HexNAc-Hex-Fuc) | 4 | 858.146 | 41.5 | 10248 | 10255 | 0.8 |
| TPLPPTSAHGNVAEGETKPDPDVTER_(2HexNAc-Hex-Fuc-Neu5Ac) | 4 | 930.922 | 44.2 | 11545 | 11560 | 0.9 |
| TPLPPTSAHGNVAEGETKPDPDVTER_(2HexNAc-Hex-Neu5Ac) | 3 | 1192.216 | 41.2 | 10110 | 10118 | 0.7 |
| TPLPPTSAHGNVAEGETKPDPDVTER_(2HexNAc-Hex-Neu5Ac) | 4 | 894.418 | 40.2 | 9653 | 9662 | 0.6 |
| TPLPPTSAHGNVAEGETKPDPDVTER_(3HexNAc-2Hex-2Neu5Ac) | 4 | 1058.470 | 43.5 | 11186 | 11209 | 0.7 |
| TPLPPTSAHGNVAEGETKPDPDVTER_(3HexNAc-3Hex) | 4 | 953.437 | 32.9 | 6146 | 6147 | 1.0 |
| TPLPPTSAHGNVAEGETKPDPDVTER_(3HexNAc-3Hex-2Fuc-2Neu5Ac) | 3 | 1562.340 | 42.6 | 10816 | 10818 | 0.7 |
| TPLPPTSAHGNVAEGETKPDPDVTER_(3HexNAc-3Hex-2Fuc-2Neu5Ac) | 4 | 1171.758 | 45.5 | 12123 | 12138 | 1.1 |
| TPLPPTSAHGNVAEGETKPDPDVTER_(3HexNAc-3Hex-2Neu5Ac) | 3 | 1464.969 | 38.2 | 8715 | 8736 | 0.9 |
| TPLPPTSAHGNVAEGETKPDPDVTER_(3HexNAc-3Hex-2Neu5Ac) | 4 | 1098.981 | 38.6 | 8894 | 8896 | 0.7 |
| TPLPPTSAHGNVAEGETKPDPDVTER_(3HexNAc-3Hex-2Neu5Ac) | 5 | 879.389 | 38.2 | 8692 | 8706 | 0.7 |
| TPLPPTSAHGNVAEGETKPDPDVTER_(3HexNAc-3Hex-3Neu5Ac) | 3 | 1562.008 | 43.2 | 11083 | 11097 | 0.7 |
| TPLPPTSAHGNVAEGETKPDPDVTER_(3HexNAc-3Hex-3Neu5Ac) | 4 | 1171.759 | 43.7 | 11306 | 11314 | 0.8 |
| TPLPPTSAHGNVAEGETKPDPDVTER_(3HexNAc-3Hex-3Neu5Ac) | 5 | 937.607 | 42.7 | 10840 | 10854 | 0.8 |
| TPLPPTSAHGNVAEGETKPDPDVTER_(3HexNAc-3Hex-4Neu5Ac) | 4 | 1244.533 | 47.2 | 12842 | 12844 | 0.7 |
| TPLPPTSAHGNVAEGETKPDPDVTER_(3HexNAc-3Hex-4Neu5Ac) | 5 | 995.829 | 46.8 | 12688 | 12689 | 0.9 |
| TPLPPTSAHGNVAEGETKPDPDVTER_(3HexNAc-3Hex-5Neu5Ac) | 4 | 1317.307 | 51.8 | 14344 | 14350 | 2.7 |
| TPLPPTSAHGNVAEGETKPDPDVTER_(3HexNAc-3Hex-Fuc-3Neu5Ac) | 4 | 1208.272 | 43.5 | 11212 | 11228 | 1.8 |
| TPLPPTSAHGNVAEGETKPDPDVTER_(3HexNAc-3Hex-Fuc-3Neu5Ac) | 5 | 966.820 | 43.5 | 11212 | 11220 | 0.7 |
| TPLPPTSAHGNVAEGETKPDPDVTER_(3HexNAc-3Hex-Neu5Ac) | 3 | 1367.944 | 35.1 | 7196 | 7215 | 1.6 |
| TPLPPTSAHGNVAEGETKPDPDVTER_(3HexNAc-3Hex-Neu5Ac) | 4 | 1026.210 | 35.1 | 7196 | 7198 | 0.7 |
| TPLPPTSAHGNVAEGETKPDPDVTER_(4HexNAc-4Hex-4Neu5Ac) | 4 | 1335.815 | 46.3 | 12473 | 12487 | 2.5 |
| TPLPPTSAHGNVAEGETKPDPDVTER_(4HexNAc-4Hex-4Neu5Ac) | 5 | 1068.852 | 44.6 | 11755 | 11764 | 1.5 |

| O-Glycopeptides | M-score | S-score | Y-Score | MS RT | Three TIQ |
|---|---|---|---|---|---|
| TPLPPTSAHGNVAEGETKPDPDVTER_(HexNAc) | 1.9 | N/A | 77.9 | 38.5 | 231629754 |
| TPLPPTSAHGNVAEGETKPDPDVTER_(HexNAc-Hex) | 2.2 | N/A | 82.4 | 35.3 | 192574557 |
| TPLPPTSAHGNVAEGETKPDPDVTER_(HexNAc-Hex) | 2.2 | N/A | 78.5 | 35.3 | 2437221120 |
| TPLPPTSAHGNVAEGETKPDPDVTER_(HexNAc-Hex-Neu5Ac) | 2.3 | N/A | 79.9 | 38.5 | 2198194752 |
| TPLPPTSAHGNVAEGETKPDPDVTER_(HexNAc-Hex-Neu5Ac) | 2.2 | N/A | 74.6 | 38.5 | 15466424704 |
| TPLPPTSAHGNVAEGETKPDPDVTER_(2HexNAc-2Hex) | 2.2 | N/A | 87.2 | 33.8 | 27053351 |
| TPLPPTSAHGNVAEGETKPDPDVTER_(2HexNAc-2Hex) | 2.3 | N/A | 77.2 | 33.8 | 431081292 |
| TPLPPTSAHGNVAEGETKPDPDVTER_(2HexNAc-2Hex-2Fuc-Neu5Ac) | 2.1 | N/A | 71.7 | 42.0 | 3954063568 |
| TPLPPTSAHGNVAEGETKPDPDVTER_(2HexNAc-2Hex-2Neu5Ac) | 2.3 | N/A | 83.6 | 41.0 | 573427140 |
| TPLPPTSAHGNVAEGETKPDPDVTER_(2HexNAc-2Hex-2Neu5Ac) | 2.1 | N/A | 77.2 | 41.0 | 6377947360 |
| TPLPPTSAHGNVAEGETKPDPDVTER_(2HexNAc-2Hex-2Neu5Ac) | 1.9 | N/A | 72.4 | 40.9 | 192706316 |
| TPLPPTSAHGNVAEGETKPDPDVTER_(2HexNAc-2Hex-3Neu5Ac) | 1.9 | N/A | 75.0 | 44.0 | 639218652 |
| TPLPPTSAHGNVAEGETKPDPDVTER_(2HexNAc-2Hex-3Neu5Ac) | 1.9 | N/A | 73.3 | 44.0 | 56253145 |
| TPLPPTSAHGNVAEGETKPDPDVTER_(2HexNAc-2Hex-4Neu5Ac) | 1.7 | N/A | 75.2 | 47.5 | 37355083 |
| TPLPPTSAHGNVAEGETKPDPDVTER_(2HexNAc-2Hex-4Neu5Ac) | 1.6 | N/A | 72.4 | 47.5 | 7263807 |
| TPLPPTSAHGNVAEGETKPDPDVTER_(2HexNAc-2Hex-Neu5Ac) | 2.4 | N/A | 85.6 | 37.1 | 50840529 |
| TPLPPTSAHGNVAEGETKPDPDVTER_(2HexNAc-2Hex-Neu5Ac) | 2.4 | N/A | 77.3 | 37.1 | 772775072 |
| TPLPPTSAHGNVAEGETKPDPDVTER_(2HexNAc-2Hex-Neu5Ac) | 2.3 | N/A | 69.5 | 37.0 | 5568842 |
| TPLPPTSAHGNVAEGETKPDPDVTER_(2HexNAc-Hex-2Neu5Ac) | 2.2 | N/A | 75.5 | 43.9 | 5861588 |
| TPLPPTSAHGNVAEGETKPDPDVTER_(2HexNAc-Hex-Fuc) | 2.0 | N/A | 64.2 | 38.6 | 1828656880 |
| TPLPPTSAHGNVAEGETKPDPDVTER_(2HexNAc-Hex-Fuc-Neu5Ac) | 1.7 | N/A | 59.4 | 42.7 | 313889802 |
| TPLPPTSAHGNVAEGETKPDPDVTER_(2HexNAc-Hex-Neu5Ac) | 2.4 | N/A | 81.6 | 40.9 | 17610932 |
| TPLPPTSAHGNVAEGETKPDPDVTER_(2HexNAc-Hex-Neu5Ac) | 2.4 | N/A | 77.3 | 40.9 | 49380856 |
| TPLPPTSAHGNVAEGETKPDPDVTER_(3HexNAc-2Hex-2Neu5Ac) | 2.4 | N/A | 78.5 | 42.8 | 10095801 |
| TPLPPTSAHGNVAEGETKPDPDVTER_(3HexNAc-3Hex) | 2.3 | N/A | 78.5 | 32.1 | 45935472 |
| TPLPPTSAHGNVAEGETKPDPDVTER_(3HexNAc-3Hex-2Fuc-2Neu5Ac) | 2.2 | N/A | 72.9 | 45.3 | 368324 |
| TPLPPTSAHGNVAEGETKPDPDVTER_(3HexNAc-3Hex-2Fuc-2Neu5Ac) | 2.3 | N/A | 62.6 | 45.3 | 10605150 |
| TPLPPTSAHGNVAEGETKPDPDVTER_(3HexNAc-3Hex-2Neu5Ac) | 2.3 | N/A | 76.5 | 38.1 | 1514594 |
| TPLPPTSAHGNVAEGETKPDPDVTER_(3HexNAc-3Hex-2Neu5Ac) | 2.3 | N/A | 77.6 | 38.4 | 192391058 |
| TPLPPTSAHGNVAEGETKPDPDVTER_(3HexNAc-3Hex-2Neu5Ac) | 2.2 | N/A | 63.8 | 38.2 | 2444823 |
| TPLPPTSAHGNVAEGETKPDPDVTER_(3HexNAc-3Hex-3Neu5Ac) | 2.3 | N/A | 77.0 | 43.2 | 22270832 |
| TPLPPTSAHGNVAEGETKPDPDVTER_(3HexNAc-3Hex-3Neu5Ac) | 2.1 | N/A | 75.4 | 42.8 | 861390400 |
| TPLPPTSAHGNVAEGETKPDPDVTER_(3HexNAc-3Hex-3Neu5Ac) | 1.7 | N/A | 71.9 | 42.8 | 178344960 |
| TPLPPTSAHGNVAEGETKPDPDVTER_(3HexNAc-3Hex-4Neu5Ac) | 1.9 | N/A | 72.7 | 47.2 | 37061631 |
| TPLPPTSAHGNVAEGETKPDPDVTER_(3HexNAc-3Hex-4Neu5Ac) | 1.6 | N/A | 65.6 | 47.1 | 12279873 |
| TPLPPTSAHGNVAEGETKPDPDVTER_(3HexNAc-3Hex-5Neu5Ac) | 2.3 | N/A | 61.0 | 52.0 | 1637785 |
| TPLPPTSAHGNVAEGETKPDPDVTER_(3HexNAc-3Hex-Fuc-3Neu5Ac) | 2.1 | N/A | 69.0 | 43.3 | 4669822 |
| TPLPPTSAHGNVAEGETKPDPDVTER_(3HexNAc-3Hex-Fuc-3Neu5Ac) | 2.5 | N/A | 73.0 | 43.4 | 639563 |
| TPLPPTSAHGNVAEGETKPDPDVTER_(3HexNAc-3Hex-Neu5Ac) | 2.3 | N/A | 77.8 | 35.3 | 8242920 |
| TPLPPTSAHGNVAEGETKPDPDVTER_(3HexNAc-3Hex-Neu5Ac) | 2.2 | N/A | 77.7 | 35.2 | 109264811 |
| TPLPPTSAHGNVAEGETKPDPDVTER_(4HexNAc-4Hex-4Neu5Ac) | 2.3 | N/A | 61.5 | 44.9 | 8489955 |
| TPLPPTSAHGNVAEGETKPDPDVTER_(4HexNAc-4Hex-4Neu5Ac) | 2.0 | N/A | 65.0 | 44.8 | 4235244 |

The results above showed similar qualitative and quantitative distributions as the reference [Miloslav Sanda, et al., Increased sialylation of site specific O-glycoforms of hemopexin in liver disease. *Clin Proteom*, 2016, 13:24]. It was also confirmed from the results of the analysis performed with hemopexin, the standard glycoprotein samples, that TPLPPTSAHGNVAEGE TKPDPDVTER(2HexNAc-2Hex) (SEQ. ID. NO: 1), the O-linked glycopeptide having the same molecular weight, could be identified in the form of A) T(HexNAc-Hex)PLPPT(HexNAc-Hex)SAHGNVAE-GETKPDPDVTER or B) T(2HexNAc-2Hex)PLPPT-SAHGNVAEGETKPDPDVTER having sugar chains bound to different O-glycosylation sites in different forms (FIGS. 8 and 9).

In conclusion, the method of the present invention is useful for the identification of O-linked glycopeptide specifically in a standard glycoprotein sample and for the quantitative analysis thereof. This method can be broadly applied to various studies in relation to the analysis of glycoprotein including biosimilars.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Human Serum Sample

The human serum sample was purchased from Sigma Aldrich. Trypsin was added to the purchased serum sample, followed by hydrolysis at 37° C. for overnight. The hydrolyzed sample was concentrated by using ZIC-HILIC column.

Example 2: Qualitative and Quantitative Analysis of O-Linked Glycopeptide

LC/ESI-MS/MS analysis was performed with Orbitrap Fusion lumos (Orbitrap Fusion™), the high resolution mass spectrometer, linked to the polypeptide included in the sample prepared in Example 1. The analysis above was repeated three times for obtaining reproducible results. The mass analysis result file (RAW) was converted into ms1 (MS) and ms2 (MS/MS) files by using RAWConverter v1.1 (The Scripps Research Institute, USA) which is a freeware program. The identification and quantification of O-linked glycopeptide were performed by the bioinformation processing analysis method for the identification and quantification of O-linked glycopeptide of the invention. The results are shown in FIGS. 10-13.

As shown in FIG. 10, the results of the qualitative analysis of O-linked glycopeptide repeated three times using the human serum sample were confirmed (FIG. 10*a*) and the results are shown in a graph (FIG. 10*b*). As shown in FIG. 11, the results obtained from the analysis of glycoprotein (FIG. 11*a*) or O-linked glycopeptide (FIG. 11*b*) were presented as Venn diagram. As shown in FIG. 12, the results of the quantification of O-linked glycopeptide repeated three times using the human serum sample were confirmed by heatmap (FIG. 12). In addition, as shown in FIG. 11, it was confirmed that the representative O-linked glycopeptide of the human serum sample analyzed by the method of the present invention displayed similar HCD, CID, and ETD spectra to those of T(HexNAc-Hex-Neu5Ac)PLPPT-SAHGNVAEGETKPDPDVTER, the representative O-linked glycopeptide of the standard protein sample (FIG. 13).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A bioinfomatic analysis method for the identification and quantification of O-linked glycopeptides comprising the following steps:

1) obtaining mass spectrum by a high resolution mass spectrometer for a glycopeptide obtained by enzyme hydrolysis of a glycoprotein in a sample;

2) converting the mass spectrum results obtained in step 1) into MS and tandem (MS/MS) spectra;

3) calculating an M-score of each tandem spectrum by using oxonium ion peaks composed of m/z of an HCD-MS/MS individual spectrum peak converted in step 2) of 126.05, 129.06, 138.06, 144.06, 145.05, 147.07, 163.06, 168.07, 186.08, 204.08, 274.09, 292.10, 350.15, 366.14, 454.16, 528.19, and 657.24, wherein the M-score is calculated by mathematical formula 1 below:

[Mathematical Formula 1]

$$M_{score} = \frac{n}{N} \times \frac{\sqrt{\sum_{i=1}^{n} O_i}}{(n-1)}, \text{ where } O_i = \frac{I_{mi} \times I_{max(\leq 700Da)}^{-1} \times C}{|MassError| + 1.0}$$

wherein, N is the number of confirmable oxonium ion peaks, n is the number of confirmed oxonium ion peaks, $I_{mi}$ is the matched $i^{th}$ peak intensity, $I_{max}$ is the intensity of the base peak in the spectrum, and C is a constant value;

4) determining a value for separating a glycopeptide and a polypeptide using Gaussian fitting method in the M-score distribution calculated in step 3), and selecting a glycopeptide spectrum;

5) selecting an O-linked glycopeptide spectrum by using O-linked and N-linked sorting factors (O/N sorting factors) from the glycopeptide spectrum selected in step 4);

6) obtaining an isotope distribution in MS of the O-linked glycopeptide spectrum selected in step 5) and then determining an O-linked glycopeptide existing in a database using an S-score calculated by comparing with the database, wherein the S-score is calculated by mathematical formula 2 below:

[Mathematical Formula 2]

$$S_{score} = \left(\frac{1.0}{\left(1.0 + \sum_{i=1}^{n}(X1-Y1)_i^2\right)} * C1\right) +$$

$$\left(\frac{n\left(\sum X2Y2\right) - \left(\sum X2\right)\left(\sum Y2\right)}{\sqrt{(n\sum X2^2 - (\sum X2)^2) * (n\sum Y2^2 - (\sum Y2)^2)}} * C2\right)$$

wherein, X1 is the mass of the $n^{th}$ peak among the theoretical isotope peaks, Y1 is the mass of the $n^{th}$ peak among the experimental isotope peaks, X2 is the relative intensity of the $n^{th}$ peak among the theoretical isotope peaks, Y2 is the relative intensity of the $n^{th}$ peak among the experimental isotope peaks, C1 and C2 are constant values;

7) evaluating the O-linked glycopeptide existing in the database determined in step 6) by using a Y-score of the tandem spectrum, wherein the Y-score is calculated by mathematical formula 3 below:

[Mathematical Formula 3]

$$Y_{score} = HCD_{match} \times C1 + CID_{match}C2$$

$$HCD_{match} = \sum_{i=1}^{n} \frac{I_{mi}}{I_{max}} \bigg/ \sum_{i=1}^{n} \frac{I_{si}}{I_{max}} \times 100.0$$

$$CID_{match} = \sum_{i=1}^{n} \frac{I_{mi}}{I_{max}} \bigg/ \sum_{i=1}^{n} \frac{I_{si}}{I_{max}} \times 100.0$$

wherein, $I_{max}$ is the intensity of the base peak in the spectrum, $I_{mi}$ is the matched $i^{th}$ peak intensity, $I_{si}$ is the $i^{th}$ peak intensity, and C1 and C2 are constant values;

8) determining an O-linked glycosylation site by calculating a P-score for the O-linked glycopeptide existing in the database evaluated in step 7) and then performing quantitative analysis of the O-linked glycopeptide included in the database evaluated above, wherein the P-score is calculated by mathematical formula 4 below:

$$P_{score} = \frac{n}{N} \times \sum_{i=1}^{n} \frac{I_{mi}}{I_{max}}$$ [Mathematical Formula 4]

wherein, N is the number of peptide fragments (c, z ion) of the confirmable glycopeptide, n is the number of peptide fragments of the confirmed glycopeptide, $I_{max}$ is the intensity of the base peak in the spectrum, and $I_{mi}$ is the matched $i^{th}$ peak intensity;

9) selecting the O-linked glycopeptide that does not exist in the database by using similarity calculated by mathematical formula 6 below with the spectrum of the O-linked glycopeptide (root/seed) existing in the database quantitatively analyzed in step 8) and a spectrum of a glycopeptide that does not exist in the database;

$$SS = \frac{\sum_{i=1}^{n} S_i \times S'_i}{\sqrt{\sum_{i=1}^{n} S_i^2 \times \sum_{i=1}^{n} S'^{2}_i}}$$ [Mathematical Formula 6]

wherein, SS is similarity of two different tandem mass spectrometry spectrum peaks and mass similarity, Si is an (x, y) matrix, x is the relative intensity of the $n^{th}$ peak, y is the mass of the $n^{th}$ peak, and S'i is an (x', y') matrix, x' is the relative intensity of the $n^{th}$ peak n, y' is the mass of the $n^{th}$ peak);

10) evaluating the O-linked glycopeptide that does not exist in the database by using a Y-score of the tandem spectrum obtained from the O-linked glycopeptide confirmed not to exist in the database selected in step 9); and 11) determining an O-linked glycosylation site by calculating a P-score for the O-linked glycopeptide that does not exist in the database evaluated in step 10) and then performing quantitative analysis of the O-linked glycopeptide that does not exist in the database evaluated above.

2. The bioinfomatic analysis method for the identification and quantification of O-linked glycopeptides according to claim 1, wherein the tandem spectrum of step 3) is a CID or HCD-MS/MS spectrum.

3. The bioinfomatic analysis method for the identification and quantification of O-linked glycopeptides according to claim 1.

4. The bioinfomatic analysis method for the identification and quantification of O-linked glycopeptides according to claim 3, wherein when the S-score is calculated, similarity is measured using Pearson correlation analysis with Euclidean distance and intensity distribution using mass distribution of isotopes.

5. The bioinfomatic analysis method for the identification and quantification of O-linked glycopeptides according to claim 1, wherein the database is constructed by using a theoretical isotope distribution of the glycopeptide from the glycoprotein in step 6) and then the database is used for the identification and quantification of O-linked glycopeptide.

6. The bioinfomatic analysis method for the identification and quantification of O-linked glycopeptides according to claim 1, wherein the tandem spectrum of step 7) or step 10) is a CID or HCD-MS/MS spectrum.

7. The bioinfomatic analysis method for the identification and quantification of O-linked glycopeptides according to claim 1, wherein the tandem spectrum of step 8) or step 11) is a CID or HCD-MS/MS spectrum.

8. The bioinfomatic analysis method for the identification and quantification of O-linked glycopeptides according to claim 1, wherein the hydrolysis is performed with an enzyme selected from the group consisting of trypsin, Arg-C, Asp-N, Glu-C, Lys-C, chymotrypsin, and proteinase K.

9. The bioinfomatic analysis method for the identification and quantification of O-linked glycopeptides according to claim 1, wherein the mass spectrometer has a mass resolution of more than 10,000 and a mass accuracy of less than 50 ppm.

10. The bioinfomatic analysis method for the identification and quantification of O-linked glycopeptides according to claim 1, wherein the mass spectrometer is Orbitrap Fusion Lumos, Orbitrap Elite, or Q Exactive mass spectrometer.

11. The bioinfomatic analysis method for the identification and quantification of O-linked glycopeptides according to claim 1, wherein the quantitative analysis in step 8) or step 11) is performed by using the S-score of MS spectra.

12. The bioinfomatic analysis method for the identification and quantification of O-linked glycopeptides according to claim 1, wherein the quantitative analysis in step 8) or step 11) is performed by summing intensities of three peaks from the theoretical maximum intensity among the isotope peaks showing the intensity of the selected glycopeptide in MS spectra.

* * * * *